US006602910B2

(12) United States Patent
Levenson et al.

(10) Patent No.: US 6,602,910 B2
(45) Date of Patent: Aug. 5, 2003

(54) D-ENANTIOMER OF DFMO AND METHODS OF USE THEREFOR

(75) Inventors: Corey Levenson, San Antonio, TX (US); Ze'ev Shaked, San Antonio, TX (US)

(73) Assignee: Ilex Oncology, Inc., San Antonio, TX (US)

( * ) Notice: Subject to any disclaimer, the term of this patent is extended or adjusted under 35 U.S.C. 154(b) by 2 days.

(21) Appl. No.: 09/801,197

(22) Filed: Mar. 6, 2001

(65) Prior Publication Data

US 2002/0045663 A1 Apr. 18, 2002

Related U.S. Application Data

(60) Provisional application No. 60/187,441, filed on Mar. 7, 2000, and provisional application No. 60/215,866, filed on Jul. 1, 2000.

(51) Int. Cl.$^7$ ............................................. A61K 31/195
(52) U.S. Cl. ...................................................... 514/564
(58) Field of Search ......................................... 514/564

(56) References Cited

U.S. PATENT DOCUMENTS

| | | | |
|---|---|---|---|
| 4,330,559 A | 5/1982 | Bey et al. ................... | 424/319 |
| 4,413,141 A | 11/1983 | Bey et al. ................... | 562/561 |
| 4,499,072 A | 2/1985 | Sunkara et al. .............. | 424/85 |
| 4,859,452 A | 8/1989 | Ajani et al. ................. | 424/10 |
| 5,002,879 A | 3/1991 | Bowlin et al. ............. | 435/71.1 |
| 5,217,886 A | 6/1993 | Au et al. .................... | 435/128 |
| 6,277,411 B1 | 8/2001 | Shaked et al. ............. | 424/489 |

FOREIGN PATENT DOCUMENTS

| | | |
|---|---|---|
| WO | WO 98/14188 | 4/1998 |
| WO | WO 98/19667 | 5/1998 |
| WO | WO 98/25603 | 6/1998 |
| WO | WO 99/49859 | 10/1999 |
| WO | WO 00/69434 | 11/2000 |

OTHER PUBLICATIONS

Loprinzi and Messing, "A prospective clinical trial of difluoromethylornithine (DFMO) in patients with resected superficial bladder cancer," *J. Cell Biochem., Supp.*, 161:153–155, 1992.
Canellakis et al., "The regulation and function of ornithine decarboxylase and of the polyamines,"*Current Topics in Cellular Regulation, Academic Press*, 15:155–202, 1979.
Carbone et al., "Phase I chemoprevention study of difluoromethylornithine in subjects with organ transplants," *Cancer Epidemiology, Biomarkers & Prevention*, 10:667–661, 2001.
Creaven et al., "Evaluation of α–difluoromethylornithine as a potential chemopreventive agent: tolerance to daily oral administration in humans," *Cancer Epidemiology, Biomarkers & Prevention*, 2:243–247, 1993.

Croghan et al., "Dose–Related α–Difluoromethylornithine Ototoxicity," *Am. J. Clin. Oncol.*, 14:331–335, 1991.
Danzin and Jung, "Lack of stringent stereospecificity in the inactivation of pyridoxal phosphate–dependent enzymes by suicide–substrates," *Chemical and Biological Aspects of Vitamin $B_6$*, 377–385, 1984.
Danzin et al., "Absence of stereospecificity in the suicide inhibition of ornithine decarboxylase," *Biochemistry of Vitamin $B_6$*, 333–336, 1987.
Doyle et al., "Effects of difluoromethylornithine chemoprevention on audiometry thresholds and otoacoustic emissions," *Arch Oto. Head Neck Surg.*, 127:553–558, 2001.
Jansen et al., "An animal model of hearing loss from α–difluor5omethylornithine,"*Arch Otolaryngol Head Neck Surg.*, 115:1234–1237, 1989.
Love et al., "A randomized, placebo–controlled trial of low–dose α–difluoromethylornithine in individuals at risk for colorectal cancer," *Cancer Epidemiology, Biomarkers & Prevention*, 7:989–992, 1998.
Marks et al., "The effects of DFMO on polyamine metabolism in the inner ear," *Hear. Res.*, 53(2):230–236, 1991.
McWilliams et al., "Characterization of the ototoxicity of difluoromethylornithine and its enantiomers," *Toxicological Sciense*, 56:124–132, 2000.
Meyskens et al., "Dose de–escalation chemoprevention trial of α–difluoromethylornithine in patients with colon polyp," *J. Natl. Cancer Inst*, 86(15):1122–1130, 1994.
Meyskens Jr. and Gerner, "Development of difluoromethylornithine (DFMO) as a chemoprevention agent," *Clinical Cancer Research*, 5:945–951, 1999.
Meyskens, Jr. and Gerner, "Development of difluoromethylornithine as a chemoprevention agent for the management of colon cancer," *J. Cell. Bio.*, 22:126–131, 1995.
Pasic et al., "α–Difluoromethylornithine ototoxicity: chemoprevention clinical trial results," *Arch. Otolaryngol. Head Neck Surg.*, 123(12):1281–1286, 1997.
Salzer et al., "Cochlear damage and increased threshold in α–difluoromethylornithine (DFMO) treated guinea pigs," *Hear. Res.*, 46:101–112, 1990.
Schweitzer et al., "Identification of polyamines in the cochlea of the rat and their potential role in hearing," *Brain Research Bulletin*, 16:215–218, 1986.

(List continued on next page.)

*Primary Examiner*—Jerome D. Goldberg
(74) *Attorney, Agent, or Firm*—Fulbright & Jaworski L.L.P.

(57) ABSTRACT

The present invention concerns a method for preventing and/or treating cancer in a patient comprising administering an effective amount of substantially purified D enantiomer of difluoromethylornithine (D-DFMO) or an analog of D-DFMO to the patient. D-DFMO or an analog thereof is administered at a dose of about 0.05 to about 20.0 gm/M$^2$/day. D-DFMO or an analog thereof may be administered more than once for the treatment and/or prevention of cancer. Methods of administration as well as compositions and formulations of substantially purified D-DFMO and analogs of D-DFMO are described.

33 Claims, 15 Drawing Sheets

OTHER PUBLICATIONS

Wagner et al., "Resolution of the enantiomers of various alpha–substituted ornithine and lysine analogs by high–performance liquid chromatography with chiral eluant and by gas chromatography on Chirasil–Val," *Anal Biochem* 164(1):102–116, 1987.

Bey et al., "Inhibition of Basic Amino Acid Decarboxylases Involved in Polyamine Biosynthesis," In: Inhibition of polyamine metabolism: biological significance and basis for new therapies. Edited by Peter McCann et al. Orlando: Academic Press, 1987.

Bitonti et al., "Catalytic Irreversible Inhibition of *Trypanosoma Brucei Brucei*Ornithine Decarboxylase by Substrate and Product Analogs and Their Effects on Murine Trypanosomiasis," *Biochemical Pharmacology*, 34(10):1773–1777, 1985.

Haegele et al., "Kinetics of α–difluoromethylornithine: An irreversible inhibitor of ornithine decarboxylase," *Clin. Pharmacol. Ther.*, 30(2):210–217, 1981.

International Patent Application Ser. No. PCT/US97/18252 filed Oct. 3, 1997.

McCann and Pegg, "Ornithine Decarboxylase as an Enzyme Target for Therapy," *Pharma. Ther.*, 54:195–215, 1992.

Metcalf et al., "Catalytic Irreversible Inhibition of Mammalian Ornithine Decarboxylase (E.C 4.1.1.17) by Substrate and Product Analogues," *J. of American Chem. Soc.*, 78:2551–2553, 1978.

U.S. Provisional application Ser. No. 60/030,266 filed Nov. 1, 1996.

D-ENANTIOMER OF DFMO AND METHODS OF USE THEREFOR

The present patent application claims priority to U.S. Provisional Patent Application Ser. No. 60/187,441 filed Mar. 7, 2000 and co-pending U.S. Provisional Patent Application Ser. No. 60/215,866 filed Jul. 1, 2000.

BACKGROUND OF THE INVENTION

1. Field of the Invention

The present invention relates generally to the fields of cancer and biology. More particularly, it concerns methods for use of the D-enantiomer of difluoromethylornithine in cancer therapy.

2. Description of Related Art

Difluoromethylornithine (DFMO) is an irreversible inhibitor of ornithine decarboxylase (ODC), the key enzyme in mammalian polyamine biosynthesis (Pasic et al., 1997). The two enantiomers of DFMO have been reported to differ in their ability to inhibit ODC, with the L form being more potent then the D enantiomer (Danzin et al., 1987). Although the physiologic functions of polyamines are not completely understood, it is clear that their intracellular concentration is highly regulated and that normal cell growth, replication, differentiation, secretory and repair functions require polyamines (Pegg and McCann, 1982; Oka et al., 1981; Pegg, 1986; Bachrach, 1973; Williams-Ashman and Canellakis, 1979; Thet et al., 1984; Luc and Baylin, 1984). Polyamines have been found in high levels in many tumor cells (Pasic et al., 1997) and support sustained cell growth that is essential for the multistep process of cancer development. In animal models of colon carcinogenesis, inhibition of ODC by DFMO reduces the number and size of colon adenomas and carcinomas (Meyskens and Gerner, 1995). Elevated levels of ODC have also been reported in transitional cell carcinoma of the bladder and the use of DFMO as a treatment for bladder cancer patients has been reported (Messing et al., 1995).

One of the unfortunate side effects of DFMO treatment is disruption of auditory function. Polyamines have been found in the cochlea, but their role in hearing is unknown (Schweitzer et al., 1986). A potential role of polyamines in the cochlea could be to allow interactions with hydrophobic environments, such as those occurring in membranes and they may regulate the flux of inorganic cations (Canellakis et al., 1979). Cochlear function is intimately dependent on the unique electrolytic concentration and positive polarization of the endolymph. Therefore, changes in the levels of polyamines could alter the kinetics of electrolytes that underlie the endocochlear potential and consequently affect cochlear function (Schweitzer et al., 1986).

Two types of ototoxicity are known, a vertigo-like syndrome and hearing loss (Meyskens and Gerner, 1995). As the daily dose of D,L-DFMO increases (0.5 g/m2/day to 3 g/m2/day), the magnitude and incidence of threshold shift increases, and the time until onset of the threshold shift decreases (Pasic et al., 1997). Patients with normal (threshold less than 30 dB) baseline audiograms demonstrate more hearing loss than those with abnormal (threshold greater than or equal to 30 dB) baseline audiograms at the higher frequency levels (Crogham et al., 1991). Both side effects are reversible after drug discontinuation (Meyskens and Gerner, 1995), with recovery of threshold showing no dependence on the magnitude of the threshold shift or the dose of D,L-DFMO that was administered (Pasic et al., 1997).

Development of chemotherapeutic agents with less ototoxic potential is complicated by a lack of dosage data in animal models and by uncertainty over which species are susceptible to DFMO ototoxicity. The route of DFMO administration most commonly employed has been via ingestion of adulterated drinking water. However, accurate quantitation of water intake (and thereby drug dose) has not been carried out. Weight loss is a serious consequence of such DFMO exposure (Meyskens et al., 1995), and it is not clear whether the weight loss results from subjects limiting their intake of contaminated water possibly due to factors such as taste) or from the toxic effect of the drug itself.

The models for DFMO study produce conflicting data. In the guinea pig, D,L-DFMO inhibits ODC activity in cochlear tissue and a significant depletion of cochlear polyamines results (Marks et al., 1991). Along with this, brainstem audiometry shows that treatment by water adulterated with 1% D,L-DFMO produces hearing loss accompanied by damage in the hook and first turn with a loss of hair cells in all rows. Inner hair cells are lost at a greater rate than outer hair cells (OHCs) (Salzer et al, 1990). When the rat is used as the model, the cochlear polyamines are not depleted to a level considered critical for disrupting polyamine-dependent processes in other systems. Auditory thresholds evaluated by brainstem evoked potentials remained unchanged in the D,L-DFMO treated rats (Schweitzer et al., 1986) although only a limited dose range was investigated.

There exists a need for therapeutic compositions and methods of use of those compositions for the treatment of cancer that demonstrate lower toxicities and/or other side effects.

SUMMARY OF THE INVENTION

The present invention concerns a method for preventing and/or treating cancer in a patient comprising administering an effective amount of substantially enriched D enantiomer of difluoromethylornithine (D-DFMO) or an analog thereof to the patient. D-DFMO or an analog thereof is administered at a dose of about 0.05 to about 20.0 gm/M$^2$/day. In preferred embodiments, D-DFMO is administered at a dose of about 0.1 to about 2.0 gm/M$^2$/day. D-DFMO or an analog thereof may be administered more than once for the treatment and/or prevention of cancer.

The cancer may be bladder cancer, colon cancer, breast cancer, pancreatic cancer, brain cancer, lung cancer, stomach cancer, a blood cancer, skin cancer, testicular cancer, prostate cancer, ovarian cancer, liver cancer, esophageal cancer, and any combination thereof. In preferred embodiments, the cancer is colon cancer, and may include familial adenomatous polyposis. In other preferred embodiments, the cancer is bladder cancer, and may include superficial bladder cancer. Preventing and/or treating cancer in a patient by administration of D-DFMO or an analog thereof can involve resection of a solid tumor. D-DFMO or an analog thereof may be administered prior to the resection or following the resection.

Preventing and/or treating cancer in a patient by administration of D-DFMO or an analog thereof is accomplished by a mechanism selected from inducing apoptosis, inhibiting cell division, inhibiting metastatic potential, reducing tumor burden, increasing sensitivity to chemotherapy or radiotherapy, killing a cancer cell, inhibiting the growth of a cancer cell, inducing tumor regression and any combination thereof.

Administration of D-DFMO or an analog thereof is by a route selected from oral, intravenous, intramuscular, intratumoral, intraperitoneal, intradermal, dermal, nasal, rectal, vaginal, topical, buccal, and intralymphatic administration. In preferred embodiments, DFMO is administered directly to the tumor. D-DFMO or an analog thereof may also be administered systemically, administered into the regional vasculature of the tumor, or administered into the region lymph system of said tumor. In even more preferred embodiments, D-DFMO is administered orally.

Substantially enriched means the D enantiomer comprises at least 60% by weight of the difluoromethylornithine dosage being administered, or at least 70% by weight of the difluoromethylornithine dosage being administered, or at least 80% by weight of the difluoromethylornithine dosage being administered, or at least 90% by weight of the difluoromethylornithine dosage being administered, or at least 95% by weight of the difluoromethylornithine dosage being administered, or at least 97.5% by weight of the difluoromethylornithine dosage being administered, or at least 99% by weight of the difluoromethylornithine dosage being administered. In preferred embodiments, the D enantiomer comprises at least 99.5% by weight of the difluoromethylornithine or analog dosage being administered.

The present invention also concerns a pharmaceutical composition, comprising substantially enriched D enantiomer of difluoromethylornithine (D-DFMO) or an analog thereof together with a pharmaceutically acceptable carrier. The D-DFMO pharmaceutical composition may be formulated into a unit dose for administration to a patient. The pharmaceutical formulation is in a form selected from rapid release, timed release, delayed release, sustained release, oral suspension, tablet, capsule, powder, troche, suppository, liposome, nanoparticle, inhalant, nasal solution, opthalmic solution, otic solution, irrigation solution, intravenous admixture, epidermal or transdermal solution, buccal tablet, syrup, cream, ointment, lotion, gel, emulsion, elixer, douche, enema, gargle, implant, and aerosol.

In preferred embodiments, the pharmaceutical composition of the present invention comprises at least 60% by weight D-DFMO or an analog thereof of the total DEMO or analog in the composition, or at least 70% by weight D-DFMO of the total DFMO in the composition, or at least 80% by weight D-DFMO of the total DFMO in the composition, or at least 90% by weight D-DFMO of the total DFMO in the composition, or at least 95% by weight D-DFMO of the total DFMO in the composition, or at least 97.5% by weight D-DFMO of the total DFMO in the composition, or at least 99% by weight D-DFMO of the total DFMO in the composition, or at least 99.5% by weight D-DFMO of the total DFMO in the composition.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A. ★: Control (n=3) and ■: 200 mg/kg D,L-DFMO (n=3); FIG. 2B. ★: Control (n=3) and ▼: 400 mg/kg D,L-DFMO (n=3); FIG. 2C. ★: Control (n=3) and ▲: 600 mg/kg D,L-DFMO (n=3); FIG. 2D. ★: Control (n=3) and ◆: 800 mg/kg D,L-DFMO; FIG. 2E. *: Control (n=3) and ●: 1.2 g/kg D,L-DFMO (n=2). Vertical bars are standard error (SE).

FIG. 3A. ★: Control (n=3) and ■: 200 mg/kg D,L-DFMO (n=3); FIG. 3B. ★: Control (n=3) and ▼: 400 mg/kg D,L-DFMO (n=3); FIG. 3C. ★: Control (n=3) and ▲: 600 mg/kg D,L-DFMO (n=3); FIG. 3D. ★: Control (n=3) and ◆: 800 mg/kg D,L-DFMO; FIG. 3E. ★: Control (n=3) and ●: 1.2 g/kg D,L-DFMO (n=2). Vertical bars are standard error (SE).

FIG. 5A. ★: Control (n=3) and ■: 500 mg/kg D,L-DFMO (n=5); FIG. 5B. ★: Control (n=3) and ●: 1 g/kg D,L-DFMO (n=3); FIG. 5C. ★: Control (n=3) and ▲: 2 g/kg D,L-DFMO (n=2). Vertical bars are standard error (SE).

FIG. 6A. ★: Control (n=3) and ■: 500 mg/kg D,L DFMO (n=5); FIG. 6B. ★: Control (n=3) and ●: 1 g/kg D,L-DFMO (n=3); FIG. 6C. ★: Control (n=3) and ▲: 2 g/kg D,L-DFMO (n=2). Vertical bars are standard error (SE).

FIG. 7A. 26%; FIG. 7B. 63%; FIG. 7C. 74%; FIG. 7D. 90%; FIG. 7E. CAP threshold of 1 g/kg/day D,L-DFMO (■) and average control (n=5, □); FIG. 7F. 1 $\mu$V CM iso-amplitude curve of 1 g/kg/day D,L-DFMO (●) and average control (n=5, ○).

FIG. 10A. ★: Control (n=5) and ■: 1 g/kg D,L-DFMO (n=5); FIG. 10B. ★: Control (n=5) and ●: 1 g/kg D-DFMO (n=5); FIG. 10C. ★: Control (n=5) and ▲: 1 g/kg L-DFMO (n=5). Vertical bars are standard error (SE).

DESCRIPTION OF ILLUSTRATIVE EMBODIMENTS

Figure 1:
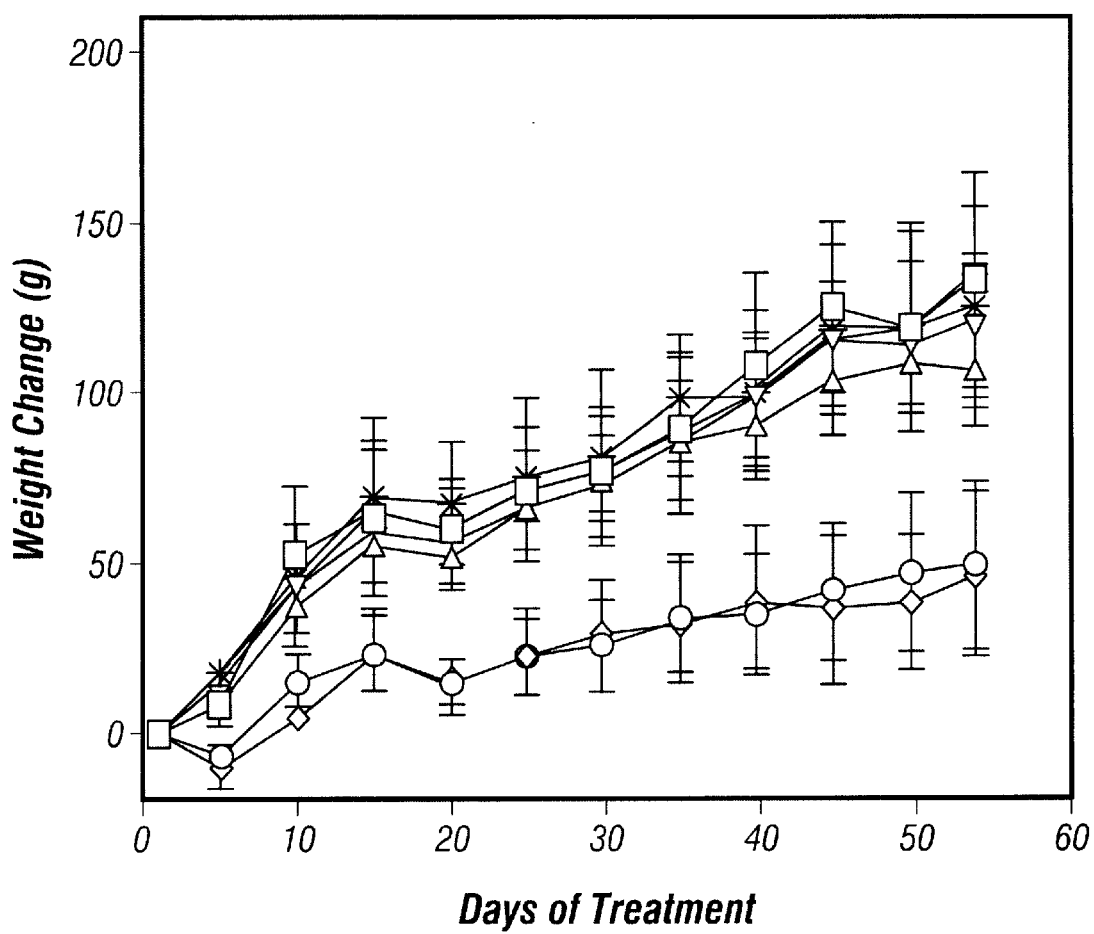
FIG. 1 Weight gain of rats treated with D,L-DFMO by gavage daily for 54 days. Four conditions were chosen to represent the data. ★: Control (n=3), ■: 200 mg/kg D,L-DFMO (n=3), ▼: 400 mg/kg D,L-DFMO (n=3); ▲: 600 mg/kg D,L-DFMO (n=3), ◆: 800 mg/kg D,L-DFMO and ●: 1.2 g/kg D,L-DFMO (n=2). Vertical bars are standard error (SE).
Figure 2A:
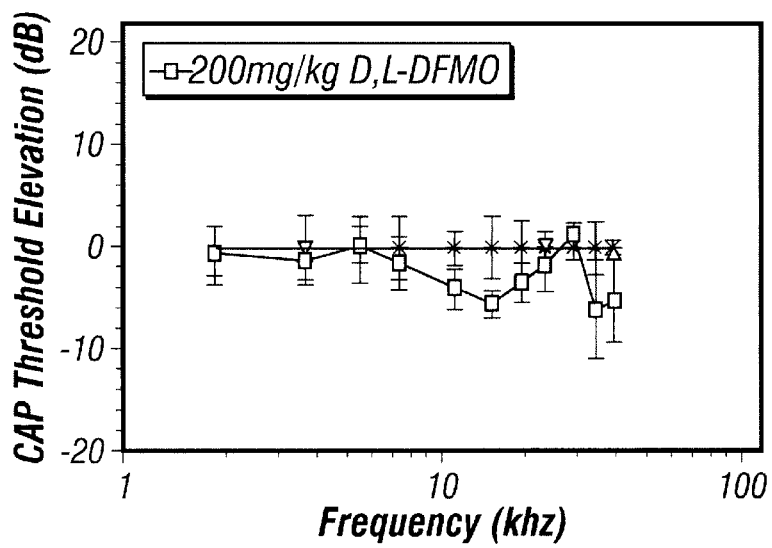
FIG. 2A, FIG. 2B, FIG. 2C, FIG. 2D, and FIG. 2E CAP threshold elevation of rats caused by 54 days of D,L-DFMO gavage. Animals are the same as in FIG. 1.
Figure 2B:
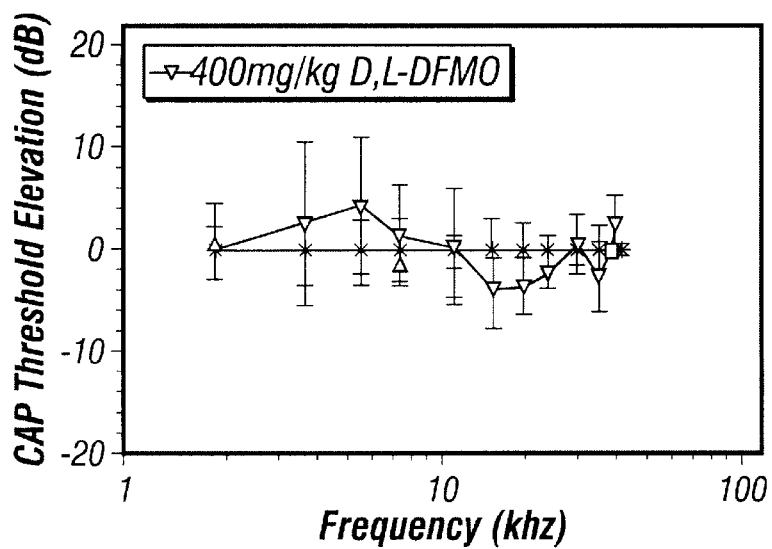
Figure 2C:
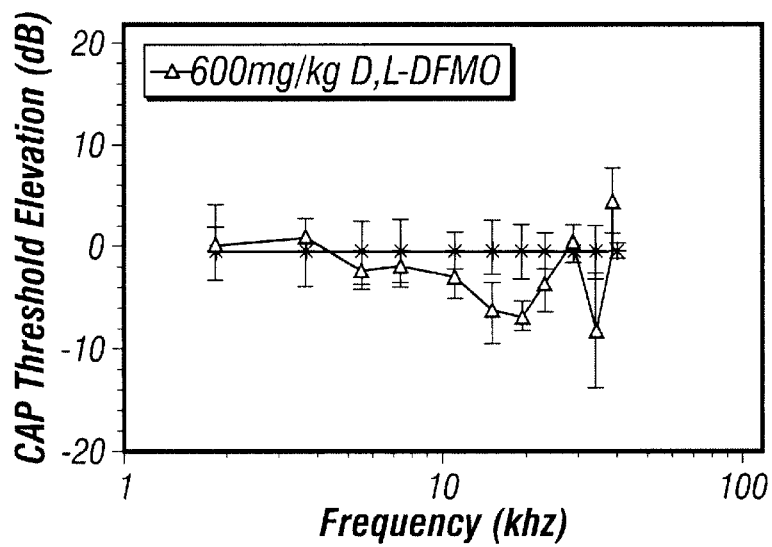
Figure 2D:
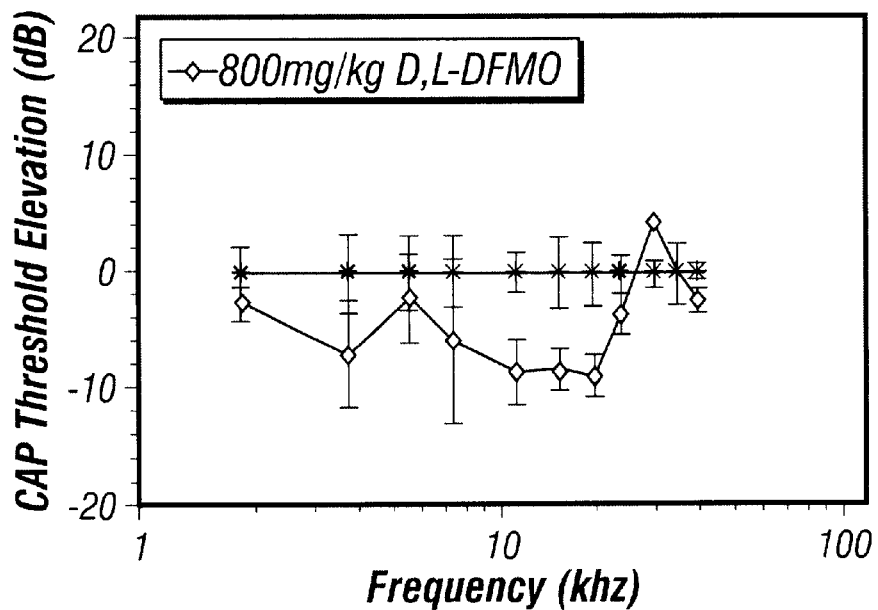
Figure 2E:
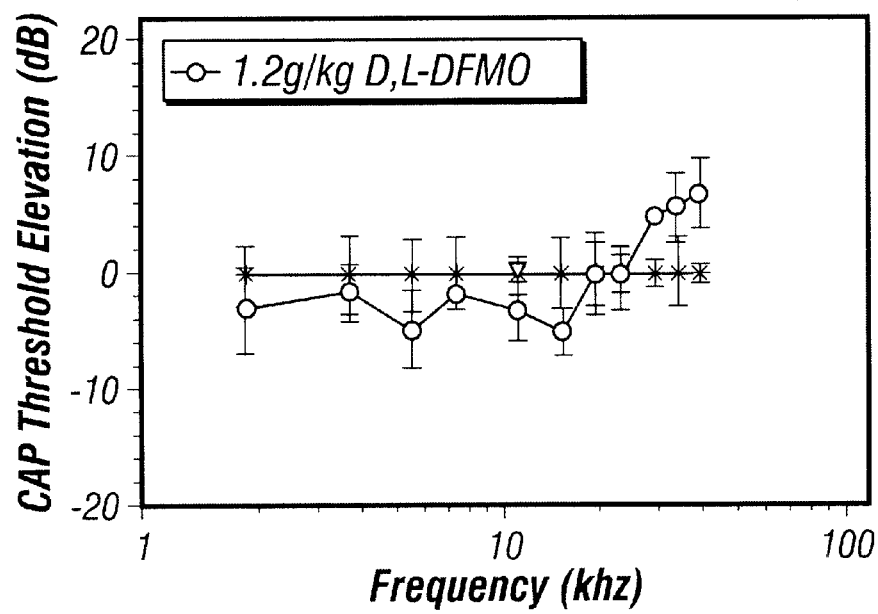
Figure 3A:
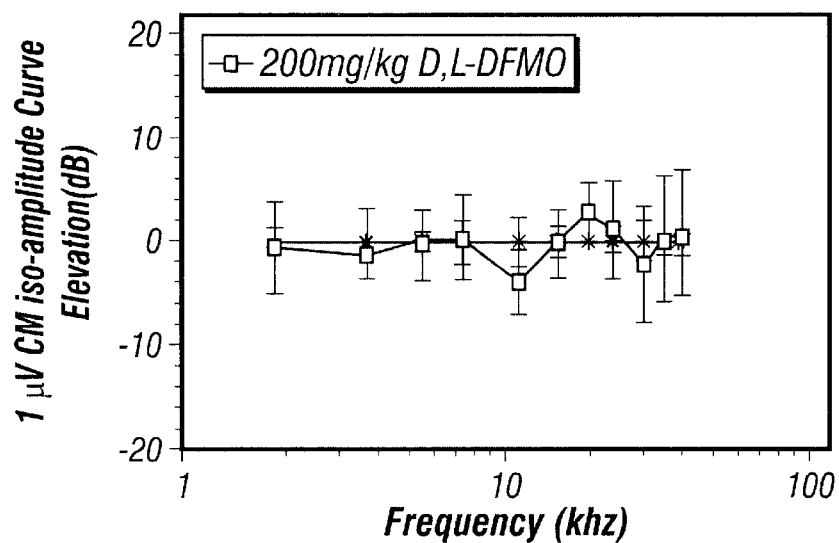
FIG. 3A, FIG. 3B, FIG. 3C, FIG. 3D, and FIG. 3E Elevations of 1 $\mu$V RMS CM iso-amplitude curve in rats caused by 54 days of D,L-DFMO gavage. Animals are the same as in FIG. 1.
Figure 3B:
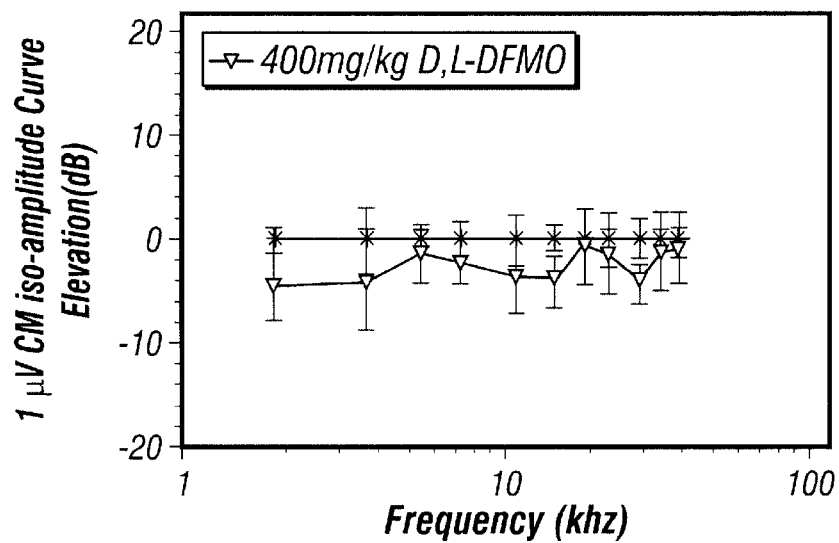
Figure 3C:
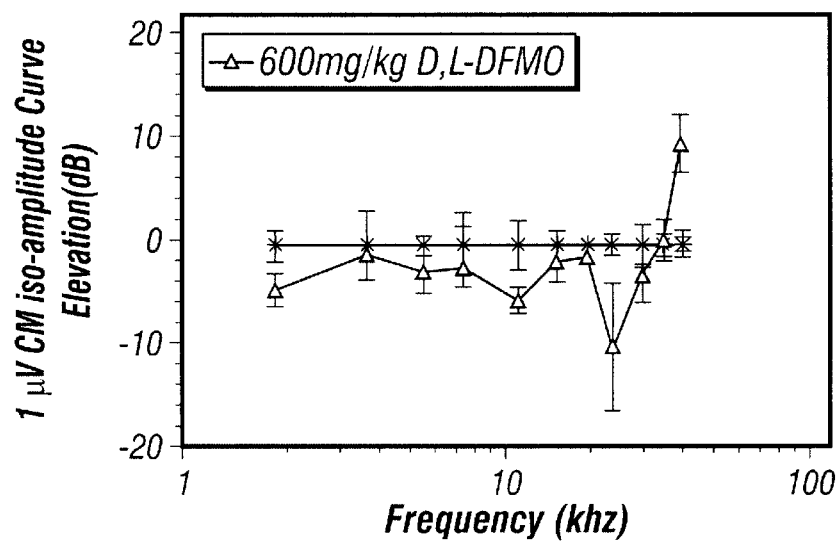
Figure 3D:
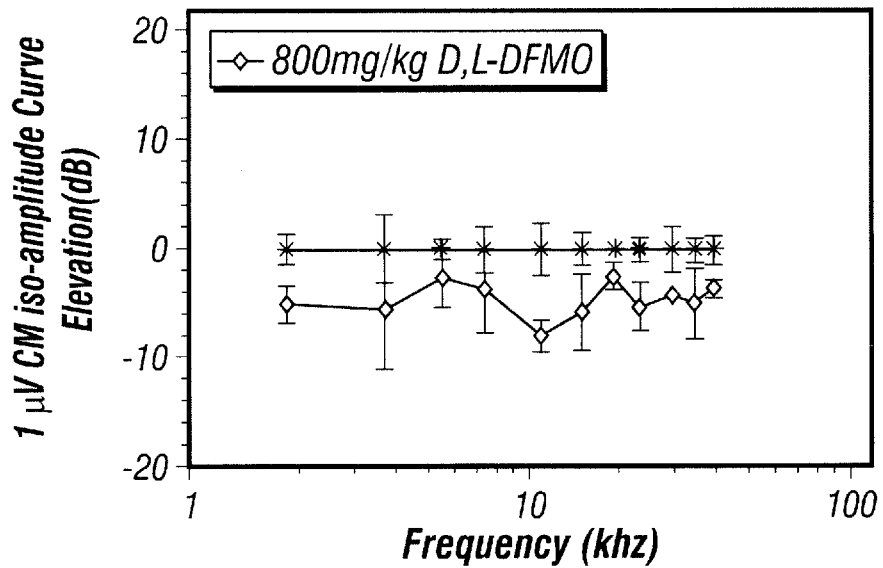
Figure 3E:
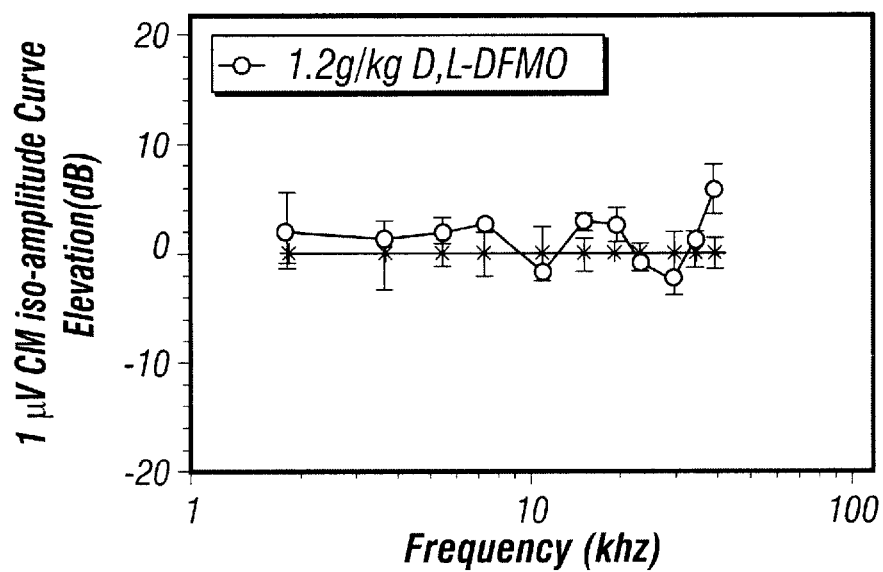

There is a need for effective and less toxic methods for preventing and/or treating cancers. Current treatment protocols, especially those for colon cancers and polyps, includes tumor resection, chemotherapy and radiation therapy. The present invention concerns the development of an effective and safe drug that will improve the prognosis of certain cancers. The present invention provides for therapeutic compositions and methods for use of the D enantiomer of difluoromethylornithine (D-DFMO) in the prevention and/or treatment of cancer.

I. Difluromethylornithine (DFMO)

D,L-DFMO, also know as eflornithine, has the chemical designation 2-(Difluoromethyl)-DL-ornithine. It is an inhibitor of ornithine decarboxylase, the rate limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents. This drug is relatively non-toxic at low doses of 0.4 gr/M$^2$/day to humans while producing inhibition of putrescine synthesis in tumors. Studies in a rat-tumor model demonstrate that D,L-DFMO infusion can produce a 90% decrease in tumor putrescine levels without suppressing peripheral platelet counts.

Analogs of D-DFMO can also be used in place of D-DFMO for the prevention and/or the treatment of cancer. The analogs will be a D isomer of the form:

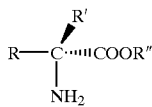

where R is a C$_{1-4}$ alkyl group or a C$_{2-4}$ alkenyl group each of which may be unsubstituted or substituted with up to 3 substituents selected from NHR''', chlorine, fluorine, OR''', or SR''' wherein R''' is hydrogen or C$_{1-4}$ alkyl; R' is a C$_{1-3}$ alkyl group substituted with up to 3 halogen atoms selected from chlorine and/or fluorine; and R'' is hydrogen or a C$_{1-4}$ alkyl group. Analogs include but are not limited to: α-methylornithine, α-ethylornithine, α-chloromethylornithine, α-fluoromethylornithine, α-difluoromethylornithine, α-dichloromethylornithine, α-chlorofluoromethylornithine, α-trifluoromethylornithine, α-trichloromethylornithine, α-dichlorofluoromethylornithine, α-chlorodifluoromethylornithine, α-ethynylornithine, α-cyanomethylornithine, α-ethylenic ornithine, α-vinylornithine, α-allenylornithine, α-hydroxymethylornithine, α-methoxymethylornithine, α-ethynyl-δ-methylornithine, α-ethynyl-δ,δ-dimethylornithine, δ-methylacetylenic ornithine, α-methyldehydroornithine, α-ethyldehydroomithine, α-chloromethyldehydroornithine, α-fluoromethyldehydroornithine, α-difluoromethyldehydroornithine, α-dichloromethydehydroornithine, α-chlorofluoromethyldehydroornithine, α-trifluoromethyldehydroornithine, α-trichloromethyldehydroornithine, α-dichlorofluoromethyldehydroornithine, αa-chlorodifluoromethyldehydroornithine, α-ethynyldehydroornithine, α-cyanomethyldehydroornithine, α-ethylenicdehydroornithine, α-vinyldehydroornithine, α-allenyldehydroornithine, α-hydroxymethyldehydroornithine, α-methoxymethyldehydroornithine, α-difluoromethylputrescine, α-fluoromethylputrescine, α-fluoromethyldehydroputrescine, δ-methyl-acetylenicputrescine, α-ethynyl-δ-methylputrescine, 3-amino-3-(methyl)-2-piperidone, 3-amino-3-(hydroxymethyl)-2-piperidone, 3-amino-3-(fluoromethyl)-2-piperidone, 3-amino-3-(chloromethyl)-2-piperidone, 3-amino-3-(difluoromethyl)-2-piperidone, α-methyllysine, α-ethyllysine, α-chloromethyllysine, α-fluoromethyllysine, α-difluoromethyllysine, α-dichloromethyllysine, α-chlorofluoromethyllysine, α-trifluoromethyllysine, α-trichloromethyllysine, α-dichlorofluoromethyllysine, α-chlorodifluoromethyllysine, α-ethynyllysine, α-cyanomethyllysine, α-ethylenic lysine, α-vinyllysine, α-allenyllysine, α-hydroxymethyllysine, α-methoxymethyllysine, α-ethynyl-δ-methyllysine, α-ethynyl-δ,δ-dimethyllysine, δ-methyl-acetylenic lysine, α-methylornithine methyl ester, α-ethylornithine methyl ester, α-chloromethylornithine methyl ester, α-fluoromethylornithine methyl ester, α-difluoromethylornithine methyl ester, α-dichloromethylornithine methyl ester, α-chlorofluoromethylornithine methyl ester, α-trifluoromethylornithine methyl ester, α-trichloromethylornithine methyl ester, α-dichlorofluoromethylornithine methyl ester, α-chlorodifluoromethylornithine methyl ester, α-ethynylornithine methyl ester, α-cyanomethylornithine methyl ester, α-ethylenic ornithine methyl ester, α-vinylornithine methyl ester, α-allenylornithine methyl ester, α-hydroxymethylornithine methyl ester, α-methoxymethylornithine methyl ester, α-ethynyl-δ-methylornithine methyl ester, α-ethynyl-δ,δ-dimethylornithine methyl ester, δ-methyl-acetylenic ornithine methyl ester, α-methylornithine ethyl ester, α-ethylornithine ethyl ester, α-chloromethylornithine ethyl ester, α-fluoromethylornithine ethyl ester, α-difluoromethylornithine ethyl ester, α-dichloromethylornithine ethyl ester, α-chlorofluoromethylornithine ethyl ester, α-trifluoromethylornithine ethyl ester, α-trichloromethylornithine ethyl ester, α-dichlorofluoromethylornithine ethyl ester, α-chlorodifluoromethylornithine ethyl ester, α-ethynylornithine ethyl ester, α-cyanomethylornithine ethyl ester, α-ethylenic ornithine ethyl ester, α-vinylornithine ethyl ester, α-allenylornithine ethyl ester, α-hydroxymethylornithine ethyl ester, α-methoxymethylornithine ethyl ester, α-ethynyl-δ-methylornithine ethyl ester, α-ethynyl-δ,δ-dimethylornithine ethyl ester, and δ-methyl-acetylenicornithine ethyl ester. A compound from the above list in which deuterium replaces hydrogen at one or more position is also considered as an analog of DFMO.

Side effects observed with D,L-DFMO include effects on hearing at high doses of 4 gr/M$^2$/day that resolve when it is discontinued. These effects on hearing are not observed at lower doses of 0.4 gr/M$^2$/day when administered for up to one year (Meyskens et al., 1994). In addition, a few cases of dizziness/vertigo are seen that resolve when the drug is stopped. Thrombocytopenia has been reported predominantly in studies using high "therapeutic" doses of D,L-DFMO (>1.0 g/m$^2$/day) and primarily in cancer patients who had previously undergone chemotherapy or patients with compromised bone marrow. Although the toxicity associated with D,L-DFMO therapy is not, in general, as severe as other types of chemotherapy, in limited clinical trials it has been found to promote a dose-related thrombocytopenia. Moreover, studies in rats have shown that continuous infusion of D,L-DFMO for 12 days significantly reduces platelet counts compared with controls. Other investigations have made similar observations, namely that thrombocytopenia is the major toxic side effect of continuous i.v. D,L-DFMO therapy. These findings suggest that D,L-DFMO may significantly inhibit ODC activity of the bone marrow precursors of megakaryocytes. DFMO may inhibit proliferative repair processes, such as epithelial wound healing.

Although D,L-DFMO can effectively block tumor putrescine biosynthesis, the resultant antitumor effect is cytostasis, not cytotoxicity. For example, D,L-DFMO reduces the growth rate of an MCA sarcoma, but does not produce tumor regression. This finding is consistent with reports of other investigators who showed that D,L-DFMO is a cytostatic agent. However, studies indicate that a significant role exists for DFMO agents, permitting the future development of combination chemotherapeutic regimens which incorporate DFMO.

D,L-DFMO and its use in the treatment of benign prostatic hypertrophy are described in two patents, U.S. Pat. Nos. 4,413,141, and 4,330,559. U.S. Pat. No. 4,413,141 describes D,L-DFMO as being a powerful inhibitor of ODC, both in vitro and in vivo. Administration of D,L-DFMO causes a decrease in putrescine and spermidine concentrations in cells in which these polyamines are normally actively produced. Additionally, D,L-DFMO has been shown to be capable of slowing neoplastic cell proliferation when tested in standard tumor models. U.S. Pat. No. 4,330,559 describes the use of D,L-DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally, or parenterally.

Because D,L-DFMO is an effective inhibitor of ODC, some researchers are attempting to use D,L-DFMO as part of a conjunctive treatment in combination with other therapeutic agents. For instance, U.S. Pat. No. 4,499,072 describes improving the polyamine-depletion effects of ODC inhibitors (including D,L-DFMO) by using interferon in combination with the ODC inhibitor. Additionally, it describes the use of both an ODC inhibitor and interferon in conjunction with a known cytotoxic agent such as methotrexate. U.S. Pat. No. 5,002,879, describe a similar conjunctive therapy in which an ODC inhibitor, preferably D,L-DFMO, is used in combination with lymphokine activated killer (LAK) cells and interleukin-2.

Alternative strategies to make D,L-DFMO more acceptable to human patients are described in U.S. Pat. No. 4,859,452. Formulations of D,L-DFMO are described which include essential amino acids in combination with either arginine or ornithine to help reduce D,L-DFMO-induced toxicities.

II. D Enantiomer of DFMO

An alternative approach for reducing toxicities associated with DFMO is described in the present invention. As described herein, the D enantiomer of DFMO and analogs thereof, while still being an inhibitor of ODC, has lower toxicity, including ototoxicity, in animal models. The use of the D enantiomer for the treatment of cancer as well as pharmaceutical compositions of D-DFMO will overcome many of the problems associated with the use of D,L-DFMO.

Wagner et al. (1987) describes a method for the resolution of the enantiomers of various alpha-substituted ornithine and lysine analogs by high-performance liquid chromatography with chiral eluant and by gas chromatography on Chirasil-Val. A reversed-phase high-performance liquid chromatography method, with L-proline and copper as chiral mobile phase, is described for the enantiomeric resolution of various alpha-substituted ornithine and lysine analogs. Although ornithine gives no separation with the chiral eluant used, excellent resolutions are obtained for various alpha-alkyl-, alpha-halogenomethyl-, alpha-vinyl-, and alpha-ethynyl-substituted ornithines, including DFMO. Similar separations are also observed for the dehydroornithine and lysine analogs. Gas chromatography on a chiral stationary phase, Chirasil-Val, allows the resolution of the ornithine and lysine analogs after derivatization into the monofluoroacyl derivatives of their corresponding lactams. No resolution, or only a poor resolution, is obtained by GC on Chirasil-Val for the dehydroornithine analogs as their di-N-perfluoroacyl alkyl esters. The chiral eluant HPLC procedure is easily scaled up for the semipreparative resolution of several ornithine analogs, i.e., alpha-fluoromethylornithine, alpha-difluoromethylornithine (DFMO), alpha-chlorofluoromethylornithine, and alpha-fluoromethyldehydroornithine, which are known as potent ornithine decarboxylase inhibitors in vitro and in vivo.

U.S. Pat. No. 5,217,886 describes a method for the production of (−)-4-difluoromethyl-ornithine (L-DFMO) by reacting a 2-substituted-piperidone with the enzyme L-α-E-aminocaprolactam-hydrolase in the presence of a divalent cation followed by purifying the L-DFMO that is produced. The enzyme is obtained from the fungus Cryptococcus laurentii Toray 2001.

U.S. Pat. No. 4,496,588 teaches a method for synthesizing the optical isomers of 2-substituted ornithines. The process comprises resolving a racemic 2-piperidone with (−) binaphthylphosphoric acid. Each of the optical isomers of the piperidone are then hydrolyzed separately to produce the desired optical isomer of the 2-substituted-ornithine.

III. Human Cancers

The present invention also involves the delivery of therapeutic compounds to individuals to reduce or inhibit cancer cells. Target cancer cells include cancers of the bladder, lung, brain, prostate, kidney, liver, ovary, breast, skin, stomach, esophagus, head and neck, testicles, colon, cervix, lymphatic system and blood. Of particular interest are epithelial cancers of many organs, including those of the colon and polyps which tend to express an activated Ki-ras. Also of particular interest is bladder cancer, including superficial bladder cancer.

The present invention also involves the delivery of therapeutic compounds to individuals exhibiting pre-cancerous symptoms to prevent the onset of cancer. Cells of this category include polyps and other precancerous lesions, premalignancies, preneoplastic or other aberrant phenotype indicating probable progression to a cancerous state.

1. Kirsten-Ras Dependent Cancers

Ras defines a protooncogene product that is found on chromosome 11. It is found in normal cells, where it helps to relay signals by acting as a switch (Lowy and Willumsen, 1993). When receptors on the cell surface are stimulated (by a hormone, for example), Ras is switched on and transduces signals that tell the cell to grow. If the cell-surface receptor is not stimulated, Ras is not activated and so the pathway that results in cell growth is not initiated. In about 30% of human cancers, Ras is mutated so that it is permanently switched on, telling the cell to grow regardless of whether receptors on the cell surface are activated or not. Point mutations in the cellular ras gene (c-ras) also can result in a mutant p21 protein that can transform mammalian cells.

Ras is a family of retrovirus-associated DNA sequences originally isolated from Harvey (H-ras, Ha-ras, rasH) and Kirsten (K-ras, Ki-ras, rasK) murine sarcoma viruses. Ras genes are widely conserved among animal species and sequences corresponding to both H-ras and K-ras genes have been detected in human, avian, murine, and non-vertebrate genomes. The closely related N-ras gene has been detected in human neuroblastoma and sarcoma cell lines. All genes of the family have a similar exon-intron structure and each encodes a p21 protein

2. Familial Adenomatous Polyposis, Syndrome, Gene

Familial Adenomatous Polyposis (FAP), an inherited polyposis syndrome, is the result of germ-line mutation of the adenomatous polyposis coli (APC) tumor suppressor gene (Su et al., 1992). This autosomal-dominant condition with variable expression is associated with the development of hundreds of colonic adenomas, which uniformly progress to adenocarcinoma by forty years of age, two decades earlier than the mean age diagnosis for sporadic colon cancer (Bussey, 1990). In prior studies of pre-symptomatic individuals with FAP, increased levels of the polyamines spermidine and spermine, and their diamine precursor putrescine, have been detected in normal-appearing colorectal biopsies when compared to normal family member controls (Giardiello et al., 1997). The activity of ornithine decarboxylase (ODC), the first and rate-limiting enzyme in mammalian polyamine synthesis, also is elevated in apparently normal colonic mucosal biopsies from FAP patients (Giardiello et al., 1997; Luk and Baylin, 1984). These findings are of interest as the polyamines are necessary for optimal cell proliferation (Pegg, 1986). Further, suppression of ODC activity, using the enzyme-activated irreversible inhibitor DFMO, inhibits colon carcinogenesis in carcinogen-treated rodents (Kingsnorth et al., 1983; Tempero et al., 1989).

The Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death.

3. Superficial Bladder Cancer

Bladder tumors are grouped into several types by the way they appear under a microscope. The three main types of cancers that affect the bladder are transitional cell carcinoma (TCC), squamous cell carcinoma, and adenocarcinoma. These same types of cancer can also develop in the lining of the kidney (called the renal pelvis), the ureters, and the urethra. In fact, it is not unusual for patients with bladder cancer to also have a similar type of cancer in the lining of the kidneys, ureters, or urethra and is why a complete evaluation of the urinary system is recommended to evaluate these patients.

Transitional cell carcinoma (TCC) is by far the most common form of bladder cancer. It accounts for about 90% of these cancers. TCCs are a cancerous version of the transitional cells that normally line the bladder. Squamous cell carcinomas account for about 8% of bladder cancers. Under a microscope, the cells look much like cells from skin cancers. Nearly all squamous cell carcinomas are invasive. Adenocarcinomas account for about 1% to 2% of bladder cancers. The cells have a lot in common with gland-forming cells of intestinal cancers. Nearly all adenocarcinomas of the bladder are invasive.

Transitional cell carcinomas, squamous cell carcinomas and adenocarcinomas all respond differently to surgery, radiation and chemotherapy—thus, treatment approaches may differ. Not all TCCs are the same; they are divided into several sub-types according to whether they are superficial or invasive, and according to whether their shape is papillary or flat.

Superficial TCC has not spread into the main muscle layer of the bladder (muscularis propria). The cancer may be entirely limited to the layers of transitional cells closest to the inside of the bladder, or it may have also spread to the thin layer of connective tissue (lamina propria) just beneath the transitional cells.

Invasive TCC has spread more deeply and involves the muscle layer of the bladder and may have invaded the fatty layers outside this muscle layer.

Papillary TCCs grow into the hollow center of the bladder. They may have a narrow stalk and look like a tiny mushroom. Some papillary TCCs grow only towards the center of the bladder. These are called superficial noninvasive papillary TCCs. Others grow toward the center and also grow outward into the muscle layer of the bladder wall. These are called invasive papillary TCCs.

Flat TCCs do not grow toward the hollow part of the bladder at all. Some of these only involve the layer of cells closest to the inside or the hollow part of the bladder. These are called noninvasive flat TCCs. The medical name for noninvasive flat TCCs is flat carcinoma in situ (CIS). Some flat TCCs invade the deeper layers (away from the hollow part), particularly the muscle layer. These are called flat invasive TCCs.

IV. Methods of Treating Cancer

In a particular aspect, the present invention provides methods for the treatment of various malignancies. Treatment methods will involve treating an individual with an effective amount of a therapeutic composition containing D-DFMO or an analog thereof. An effective amount is described, generally, as that amount sufficient to detectably and repeatedly to ameliorate, reduce, minimize or limit the extent of a disease or its symptoms. More rigorous definitions may apply, including elimination, eradication or cure of disease.

An example of a preferred cancer for treatment with a therapeutic composition containing enriched D-DFMO or an analog thereof is bladder cancer, and in particular early stage or superficial bladder cancer. Early stage bladder cancer can be almost always treated without removing the bladder. Treatment options include transurethral resection (TUR) alone, or TUR followed by fulguration (burning), intravesical immunotherapy, or intravesical chemotherapy.

Partial cystectomy is rarely done for Stage 0 bladder cancer. Even more rarely is radical cystectomy done to treat this stage. This operation is considered only when there are many superficial cancers or when a superficial cancer continues to grow or is later identified in several more areas within the bladder despite other treatments.

The prognosis for people with Stage 0a bladder cancer is excellent. These noninvasive papillary cancers are nearly always cured by appropriate treatment and long-term follow-up care. Although these patients are likely to develop one or more superficial cancers elsewhere in their urinary system these new cancers are rarely deeply invasive and life threatening. The 5-year survival rate for Stage 0a cancer is better than 95%.

The prognosis for Stage 0 is bladder cancer (also known as carcinoma in situ or flat non-invasive cancer is not quite as favorable, because they have a greater risk of eventually developing into a cancer with muscle invasion. The 5-year survival rate is about 85%.

Intravesical chemotherapy means that a medication is placed directly into the bladder rather than being given by mouth or injected into a vein. When given directly into the bladder, these medications reach cancer cells near the bladder lining but do not reach cancer cells which are in the kidneys, ureters, and urethra, cancer cells which may have invaded deeply into the bladder wall, or cancer cells that have spread to other organs. For this reason, this treatment is used only for superficial (Stage 0) or minimally invasive (Stage I) bladder cancers. This treatment uses drugs that kill actively growing cancer cells. Many of the same drugs are given systemically (by mouth or into a vein) to treat more advanced stages of bladder cancer. Thiotepa, mitomycin, and doxorubicin hydrochloride are the drugs used most often for intravesical chemotherapy. One of the main advantages of intravesical chemotherapy is that the medication does not spread throughout the body. This limits the unwanted side effects to other organs that can occur with systemic chemotherapy.

D-DFMO or an analog thereof may be administered at a dose of about 0.05 to about 20.0 gm/M$^2$/day, due to lower anticipated toxicity associated with the D enantiomer. Preferred doses of D-DFMO or an analog be administered are from about 0.1 to about 15.0 gm/M$^2$/day, or from about 0.1 to 12 gm/M$^2$/day, or from about 0.1 to 10 gm/M$^2$/day, or from about 0.1 to 8 gm/M$^2$/day, or from about 0.1 to 6 gm/M$^2$/day, or from about 0.1 to 4 gm/M$^2$/day, or from about 0.1 to 2 gm/M$^2$/day, or from about 0.1 to 1 gm/M$^2$/day, or from about 0.1 to 0.5 gm/M$^2$/day.

To kill cells, inhibit cell growth, inhibit metastasis, decrease tumor size and otherwise reverse or reduce the malignant phenotype of tumor cells, using the methods and compositions of the present invention, one would generally contact a "target" cell with the therapeutic composition. This may be combined with compositions comprising other agents effective in the treatment of cancer. These compositions would be provided in a combined amount effective to kill or inhibit proliferation of the cell. This process may involve contacting the cells with D-DFMO or an analog thereof and the agent(s) or factor(s) at the same time. This may be achieved by contacting the cell with a single composition or pharmacological formulation that includes both agents, or by contacting the cell with two distinct compositions or formulations, at the same time, wherein one composition includes D-DFMO or an analog thereof and the other includes the second agent.

Alternatively, the D-DFMO therapy may precede or follow the other agent treatment by intervals ranging from minutes to weeks. In embodiments where the other agent and D-DFMO or an analog of D-DFMO are applied separately to the cell, one would generally ensure that a significant period of time did not expire between the time of each delivery, such that the agent and D-DFMO would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the therapeutic D-DFMO or an analog thereof composition of the present invention to a patient will follow general protocols for the administration of chemotherapeutics, taking into account the toxicity, if any, of D-DFMO or the analog of D-DFMO. It is expected that the treatment cycles would be repeated as necessary. It also is contemplated that various standard therapies, as well as surgical intervention, may be applied in combination with the described therapy.

Where clinical application of a D-DFMO therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Depending on the particular cancer to be treated, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

In certain embodiments, ex vivo therapies also are contemplated. Ex vivo therapies involve the removal, from a patient, of target cells. The cells are treated outside the patient's body and then returned. One example of ex vivo therapy would involve a variation of autologous bone marrow transplant (ABMT). Many times, ABMT fails because some cancer cells are present in the withdrawn bone marrow, and return of the bone marrow to the treated patient results in repopulation of the patient with cancer cells. In one embodiment, however, the withdrawn bone marrow cells could be treated while outside the patient with an viral particle that targets and kills the cancer cells. Once the bone marrow cells are "purged," they can be reintroduced into the patient.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

One of the preferred embodiments of the present invention involves the use of therapeutic compositions of D-DFMO or an analog thereof with specific target cancer cells. Target cancer cells include cancers of the lung, brain, prostate, kidney, liver, ovary, breast, skin, stomach, esophagus, head and neck, testicles, colon, cervix, lymphatic system and blood. Of particular interest are non-small cell lung carcinomas including squamous cell carcinomas, adenocarcinomas and large cell undifferentiated carcinomas.

According to the present invention, one may treat the cancer by directly injection a tumor with the D-DFMO or analog composition. Alternatively, the tumor may be infused or perfused with the composition using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The viral particles may advantageously be contacted by administering multiple injections to the tumor, spaced at approximately 1 cm intervals.

In certain embodiments, the tumor being treated may not, at least initially, be resectable. Treatments with therapeutic D-DFMO or analog compositions may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

Cancer therapies also include a variety of combination therapies with both chemical and radiation based treatments. Combination chemotherapies include, for example, cisplatin (CDDP), carboplatin, procarbazine, mechlorethamine, cyclo-phosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Various combinations may be employed, for instance where D-DFMO or analog composition is "A" and the radio- or chemotherapeutic agent is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

V. Pharmaceutical Compositions

Aqueous compositions of the present invention comprise an effective amount of D-DFMO or an analog thereof, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains an headpin agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

D-DFMO or analog of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One also may use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

In certain embodiments, the use of liposomes and/or nanoparticles is contemplated for the formulation and administration of D-DFMO or an analog thereof. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods for In Vivo Studies of DFMO

Animals and Reagents

Twenty-four Long Evans pigmented rats (250–275 g) were acquired from Harlan Sprague Dawley (Indianapolis, Ind.) and thirty-six pigmented guinea pigs obtained from Kuiper Rabbit Ranch (Gary, Ind.) at an initial weight of 200–250 g and housed in University of Oklahoma Health Sciences Center animal facility. Subjects were housed under a 12:12 hr light dark cycle with free access to food and water with a room temperature controlled at 21° C.

D,L-DFMO Dose Response in Rats

Twenty-four animals were randomly placed into 8 groups of three subjects each. Treatment groups were as follows: 0, 200, 400, and 600 mg/kg/day D,L-DFMO by gavage daily (5 days/week) for 4 and 8 weeks. Four additional animals were randomly placed into 2 subsequent groups: 400 and 600 mg/kg/day by gavage twice a day (5 days/week) for 8 weeks. For the weekend, D,L-DFMO (volume determined by weight estimation) was left in the drinking water (30 ml/day/animal). Weight measurements were taken daily (5 days/week) with assessment of auditory function performed at the conclusion of dosing.

D,L-DFMO Dose Response in Guinea Pigs

Thirty-one juvenile pigmented guinea pigs were randomly assigned to treatment groups receiving daily (7 days/week) ip injection with 0.5 g/kg D,L-DFMO (n=5), 1 g/kg/day D,L-DFMO (n=5), 2 g/kg/day D,L-DFMO (n=2), 3 g/kg/day D,L-DFMO (n=4), and saline vehicle (n=5). The variation in number of animals is due to the pronounced mortality rate, which led to the decision to discontinue addition of animals to the higher exposure groups. Auditory thresholds were assessed in the 0.5 g/kg and 1 g/kg/day subjects at day 45 of dosing while the 2 g/kg/day subjects were evaluated at 22 days of dosing. Thus, subjects in the 1 g/kg/day and 2 g/kg/day doses of D,L-DFMO received approximately identical total D,L-DFMO doses per kg body weight. Daily weight measurements determined the injection volume. Assessment of auditory function occurred at the conclusion of dosing.

DFMO Enantiomers Versus Racemate in Guinea Pigs

Twenty subjects were randomly assigned to treatment groups (n=5) that received 1 g/kg/day D-DFMO, 1 g/kg/day L-DFMO, 1 g/kg/day D,L-DFMO or saline. Injections, determined by daily weight measurements, were made ip daily for 45 days. Assessment of auditory function occurred at the conclusion of dosing with all animals surviving the trial period.

CAP and CM Recording and Analysis

At the end of the treatment cycle (24 hours after last drug dosage), the rats were anesthetized with xylazine (13 mg/kg, i.m.) and ketamine (87 mg/kg, i.m.) and guinea pigs were anesthetized with xylazine (5 mg/kg, i.m.), ketamine (30 mg/kg, i.m.), and urethane (160 mg/kg, i.p.). The round window was surgically exposed using a ventro-lateral approach and a silver wire electrode was carefully placed on the round window under a surgery microscope for recording compound action potential (CAP) and cochlear microphonic (CM). A silver chloride electrode was placed in the neck muscle as the reference. The CAP and CM signals were amplified with a Grass A. C. preamplifier (Model P15). The gain was 1000. The band-pass frequency for CAP was 0.1–1.0 kHz and 0.1–50 kHz for CM. The CAP signals were observed using a digital oscilloscope (Nicolet Instrument Co., 2090-IIIA). The CM signals were sent to a SR530 Lock-in amplifier (Stanford Research Systems, Inc.) and then to a PC computer for automatic determination of the 1 $\mu$V RMS amplitude. The sound level of test frequencies that evoked a just detectable CAP was determined and this value was used to estimate the threshold at the frequency. The sound levels that evoked 1 $\mu$V RMS CM at each test frequencies was determined by the computer program and the 1 $\mu$V RMS CM iso-amplitude curve was evaluated. CAP-threshold shifts were calculated as the difference between each CAP-threshold for each treated subject and the mean control value (from subjects exposed to vehicle alone) at the same frequency. CM iso-amplitude curve elevation was obtained in a similar way.

Pure tones for eliciting CAP and CM were generated with the SR530 Lock-in amplifier (Stanford Research Systems, Inc., Sunnyvale, Calif.). The signals were attenuated by a programmable attenuator and then amplified by a high voltage amplifier and delivered to a high frequency sound source (made from an ACO ½" microphone, 7013) placed within a speculum that fit into the exposed external auditory meatus. The frequencies of the tones were 2, 4, 6, 8, 12, 16, 20, 24, 30, 35 and 40 kHz. Continuous tones were used for eliciting CM. Tone bursts were used to elicit the CAP. The duration of the tone bursts was 10 msec with a rise/fall time of 1.0 msec, and a repetition rate of 9.7/sec. Sound levels at all testing frequencies were calibrated with a probe microphone located near the eardrum.

Repeated measures ANOVA (NCSS software) was used to evaluate the overall significance between different drug exposures and test frequencies and their interactions. Frequency was evaluated as a within subject variable and treatment group was a between subject variable. Post hoc analysis was performed by Fisher's Least Square Difference.

Histology

Surface preparations of the Organ of Corti were evaluated in a limited number of subjects. The animals were decapitated while deeply anesthetized after CAP and CM recording. Cochleae were removed immediately. Both the round and oval windows were opened and the apex of the cochlea was drilled open to facilitate perfusion. The cochleae were perfused with SDH (succinate dehydrogenase) incubative solution (0.05 M sodium succinate, 0.05 M phosphate buffer and 0.05% TetraNitro Blue Tetrazolium) and immersed in the solution for one h (37° C.). Then the cochleae were fixed with 10% formalin for at least 2 days. After fixation, the cochleae were decalcified in 10% EDTA solution (EthyleneDiamine Tetraacetic Acid) for 3 days or longer as needed. Cochlea microdissection was accomplished under a light microscope.

Example 2

Dose Response Toxicity and Ototoxicity in Rats Treated with D,L-DFMO

D,L-DFMO exposure in rats with doses between 200 mg/kg/day and 1.2 g/kg/day does not produce any significant weight change or auditory dysfunction when intubation exposures of up to eight weeks are used. FIG. 1 shows the weight gain in grams for all treatment groups averaged over five-day intervals. Compared to the weight gain of the controls, doses between 200 mg/kg/day and 600 mg/kg/day do not cause any weight loss. The two highest doses appear to reduce weight gain, although the number of subjects used in these groups was small. When subjected to statistical analysis, these data did not meet the significance criteria ($F_{[22,44]}$=1.56, p=0.103).

The effects of multiple doses of D,L-DFMO treatments on CAP threshold and CM amplitude are represented in FIG. 2 and FIG. 3, respectively. D,L-DFMO has no effect on either of the measures. CAP threshold levels and the 1 $\mu$V RMS iso-amplitude CM curve varied by less than 5 dB from vehicle treated control subjects; shifts of this magnitude are within the error associated with measurement and have no biological significance ($F_{[2,4]}$=1.24,p=0.381).

Example 3

Dose Response Toxicity and Ototoxicity in Guinea Pigs Treated with D,L-DFMO

Figure 4:
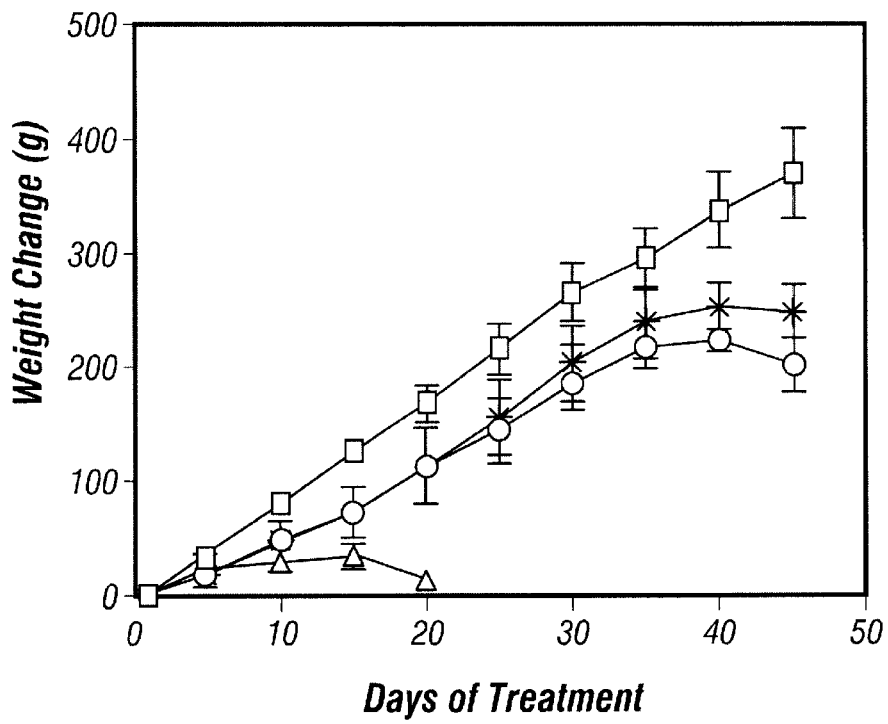
FIG. 4 Weight gain of guinea pigs treated with D,L-DFMO by ip injection daily for 45 days. 2 g/kg D,L-DFMO were terminated early due to toxicity. Data only represents animals that had auditory assessment performed. ★: Control (n=3), ■: 500 mg/kg D,L-DFMO (n=5), ●: 1 g/kg D,L-DFMO (n=3), and ▲: 2 g/kg D,L-DFMO (n=2). Vertical bars are standard error (SE).

In contrast to the data observed in rats, substantial general toxicity and ototoxicity were observed when guinea pigs were treated with doses of D,L-DFMO between 500 mg/kg/day and 3 g/kg/day. All 3 g/kg/day subjects died within the first six days of treatment and two of the five 1 g/kg/day subjects did not survive the full 6 week dosing regimen. With the loss of the 3 g/kg/day group, two 2 g/kg/day subjects were added. By day 22, the 2 g/kg/day animals had gained virtually no weight so the animals' auditory function was evaluated at this time. FIG. 4 shows the rate of weight gain of the animals for which auditory assessment was made. Weight gain was effectively blocked for the 2 g/kg/day subjects while the 1 g/kg/day subjects appear to diverge from the controls during the last 10 days of the dosing period. The 500 mg/kg/day D,L-DFMO animals showed no apparent signs of systemic toxicity; their growth rate actually surpassed that of the controls. Analysis revealed that neither the 500 mg/kg/day nor 1 g/kg/day subjects were significantly different from the control (F<1.0).

Figure 5A:
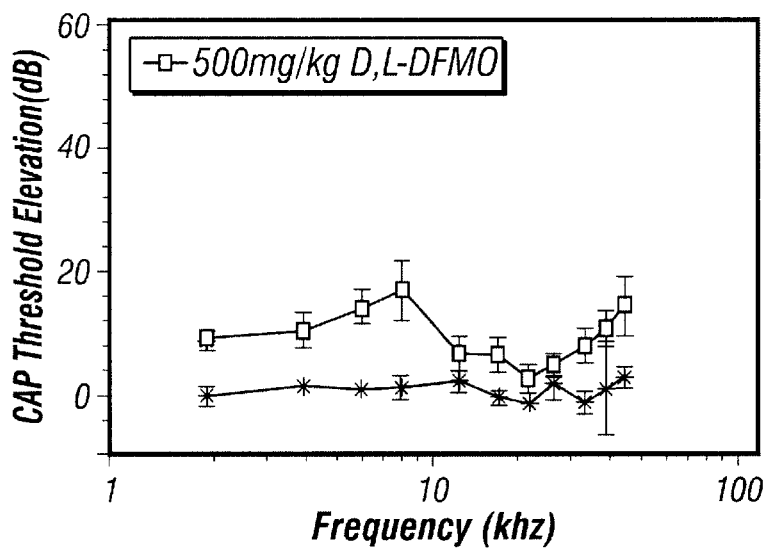
FIG. 5A, FIG. 5B, and FIG. 5C CAP threshold elevation of guinea pigs caused by treatment with D,L-DFMO by ip injection daily. Animals are the same as in FIG. 4.
Figure 5B:
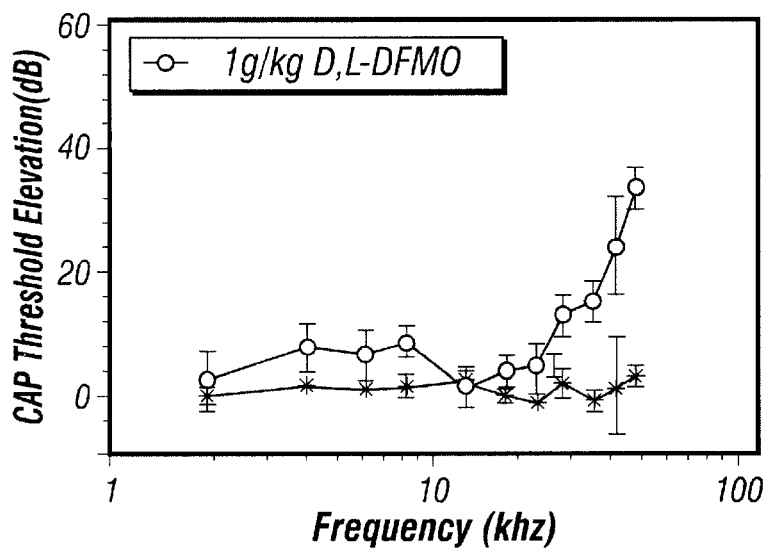
Figure 5C:
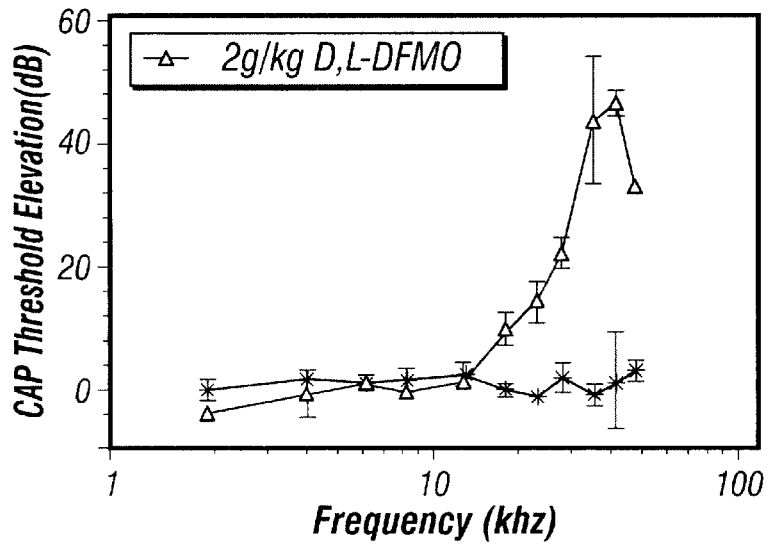

A dose dependent elevation in auditory thresholds was observed in the D,L-DFMO treated guinea pigs. Due to the general toxicity, auditory assessments was actually performed on five 500 mg/kg/day D,L-DFMO, three 1 g/kg/day D,L-DFMO, two 2 g/kg/day D,L-DFMO, and three control subjects (two subjects were dropped, one due to anaesthetic overdose and another due to pregnancy). FIG. 5 shows the loss of CAP sensitivity for each D,L-DFMO dose group. Subjects receiving 500 mg/kg/day of the drug showed a CAP threshold elevation averaging 9 dB and the loss was relatively flat across frequency. The limited number of 2 g/kg/day and 1 g/kg/day animals showed a shift in threshold that was most apparent in the high frequency test range. The 2 g/kg/day group revealed an average loss across all frequencies of 14 dB while the 1 g/kg/day subjects had a 10 dB average shift. When only the frequencies between 20 and 40 kHz were evaluated, the average loss of auditory sensitivity for the 2 g/kg/day subjects was 30 dB, compared to only 17 dB for the 1 g/kg/day subjects and 7.1 dB for the 500 mg/kg/day subjects. Repeated measures ANOVA corrected for unequal n determined a significant difference in CAP between the four dose groups receiving 2 g/kg/day D,L-DFMO, 1 g/kg/day/day D,L-DFMO, 500 mg/kg/day D,L-DFMO, and saline (between treatment, $F_{[3,9]}=4.06$, p=0.044; between frequency, $F_{[10,190]}=25.98$, p<0.001; treatment-frequency interaction, $F_{[30,190]}=10.89$, p<0.001). Post hoc analysis showed that all three drug treatments were significantly different from the control (p<0.05).

Figure 6A:
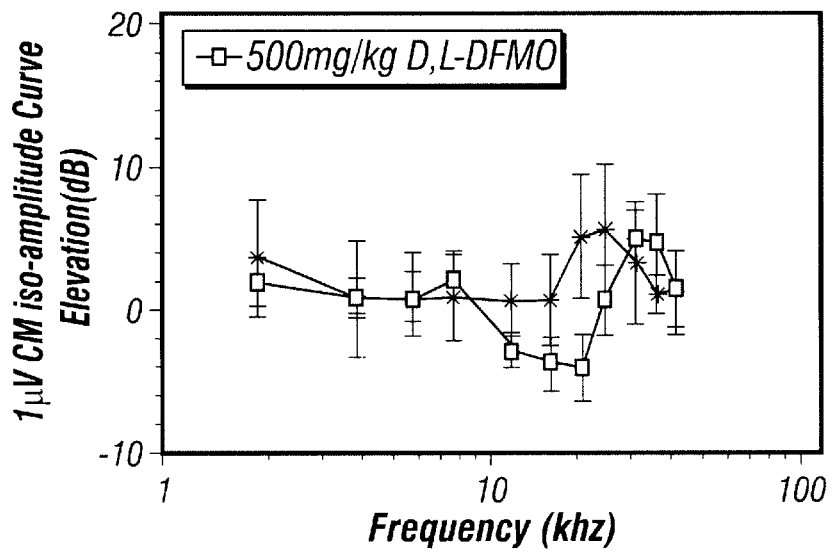
FIG. 6A, FIG. 6B, and FIG. 6C Elevations of 1 $\mu$V RMS CM iso-amplitude curve of guinea pigs caused by treatment with D,L-DFMO by ip injection daily. Animals are the same as in FIG. 4.
Figure 6B:
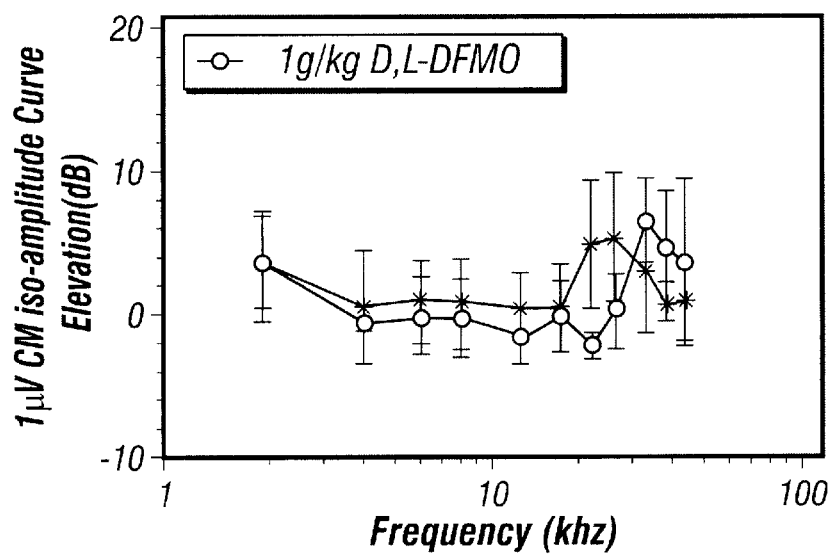
Figure 6C:
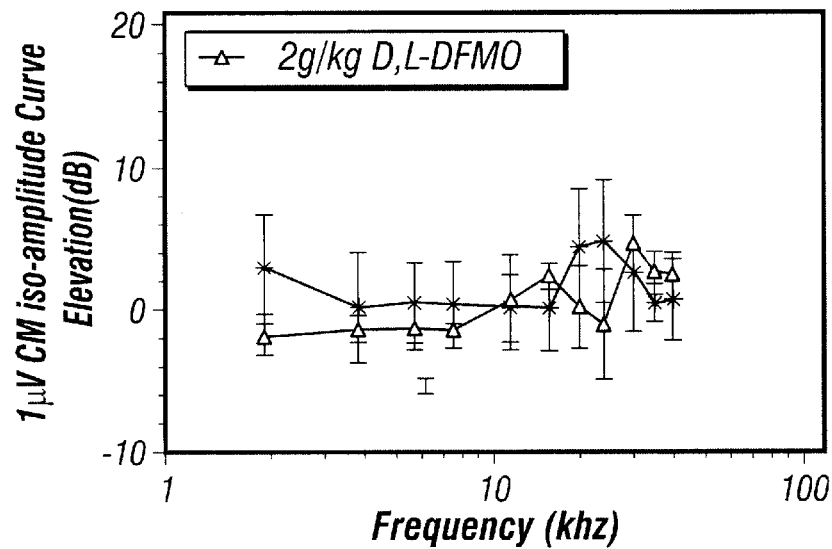

Interestingly, in contrast to the disruption in CAP sensitivity, none of the treatments had an effect on CM sensitivity (see FIG. 6). The CM is generated mainly by the outer hair cells, especially those at the base of the cochlea (close to the recording electrode), to an acoustic stimulation. The CM was not effected by any of the doses of D,L-DFMO suggesting that the effect seen in the CAP did not occur secondarily based on OHC dysfunction. None of the treatments produced changes in the CM curve that met statistical significance from the control (F<1.0).

Figure 7A:
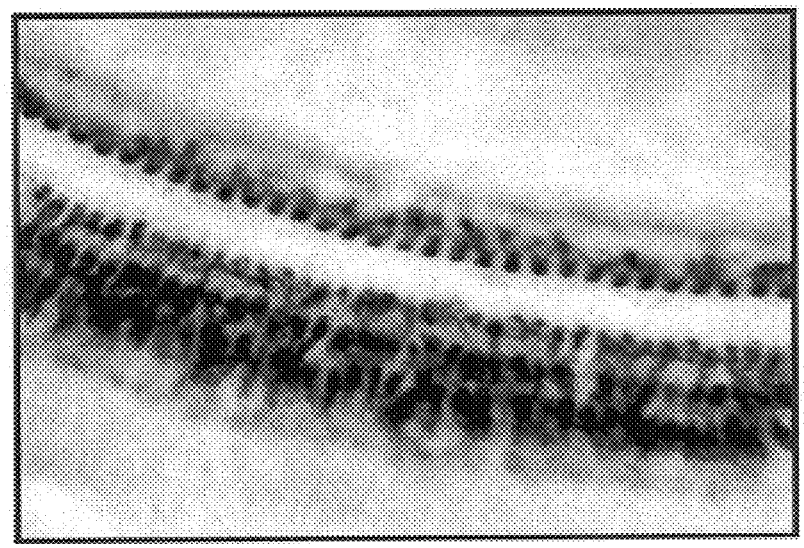
FIG. 7A, FIG. 7B, FIG. 7C, FIG. 7D, FIG. 7E, and FIG. 7F Hair cell loss and hearing loss in one animal treated with D,L-DFMO (1 g/kg/day for 45 days). Locations are percentage distance from the apex of the basilar membrane. All light micrographs are at same magnification.
Figure 7B:
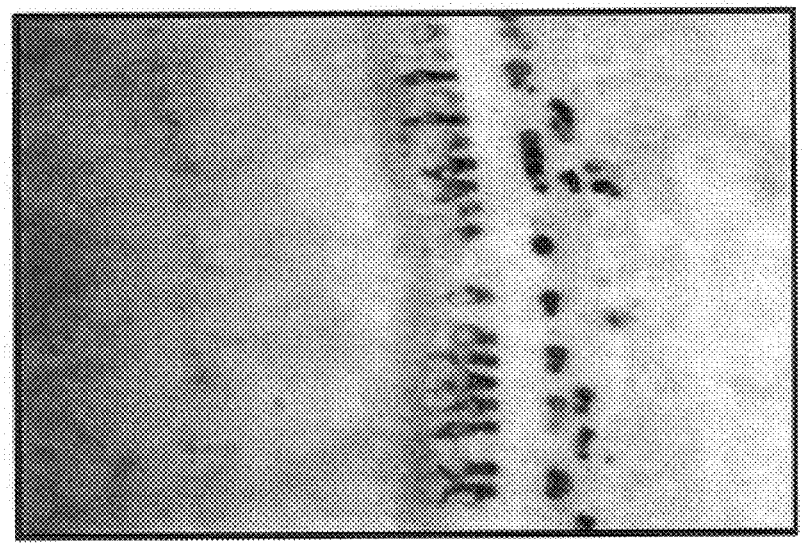
Figure 7C:
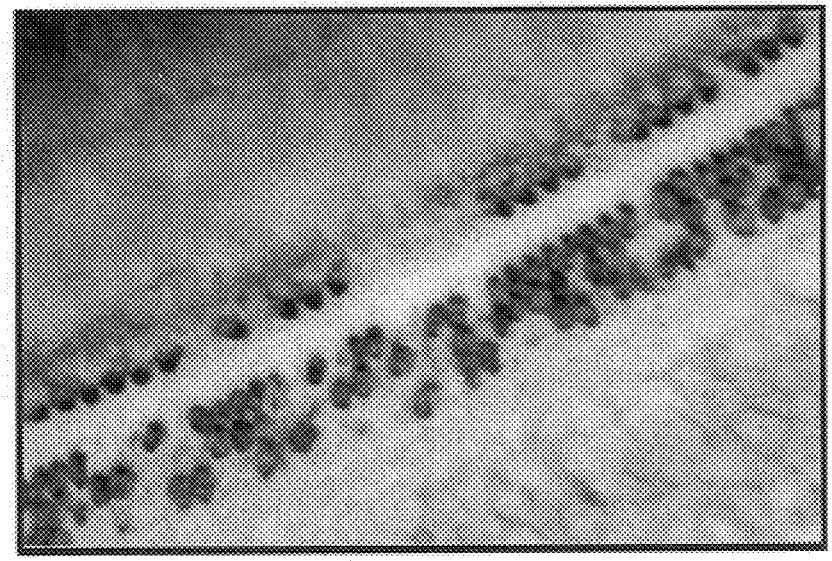
Figure 7D:
Figure 7E:
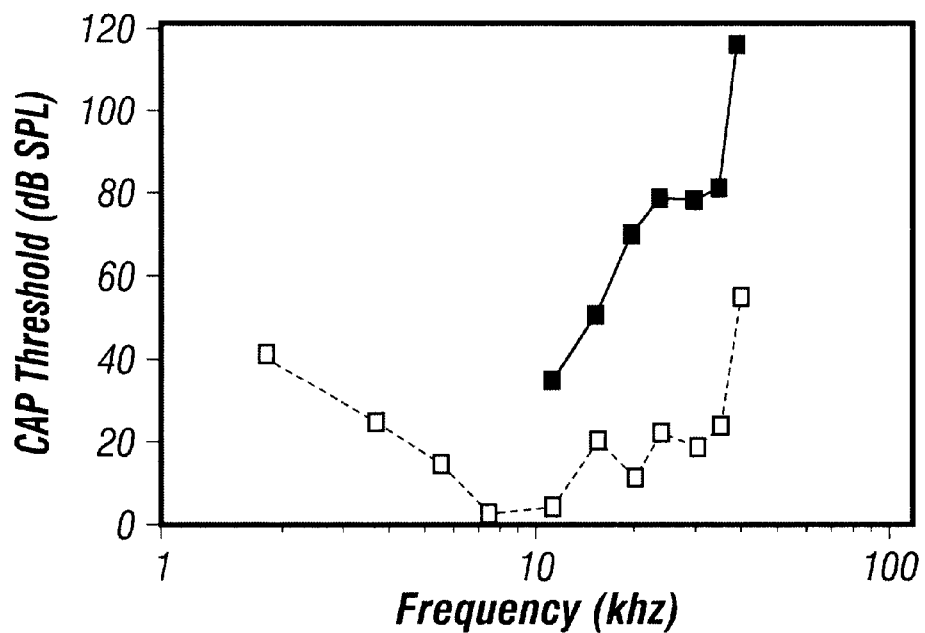
Figure 7F:
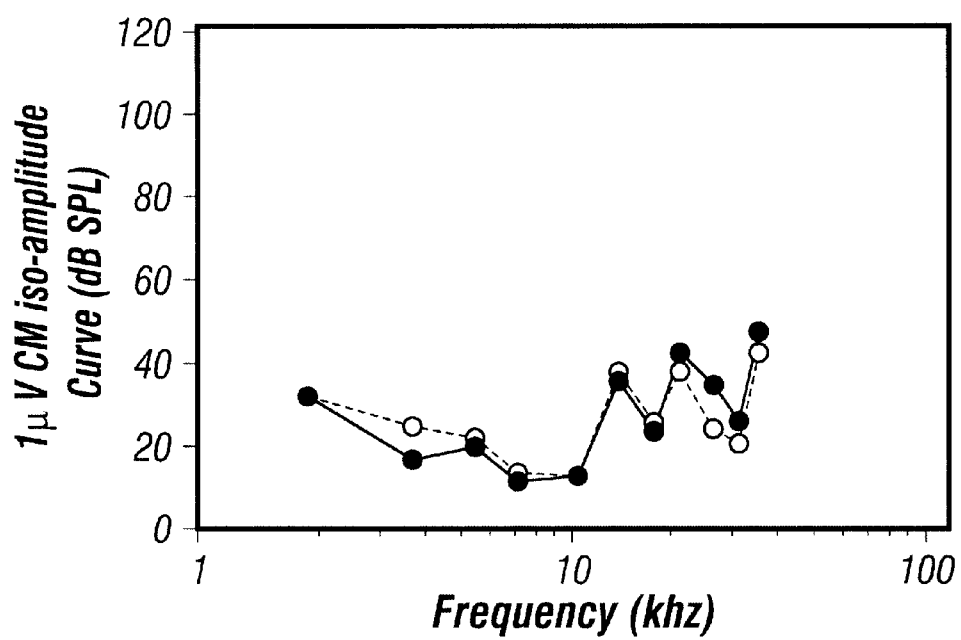

Hair cell damage was examined histologically in a guinea pig with severe CAP threshold elevation caused by D,L-DFMO (1 g/kg/day for 45 days), but with no change in CM sensitivity. This subject's CAP threshold loss relative to control increased with stimulus frequency, with the highest elevation of 55 dB at 40 kHz (FIG. 7E). CAP thresholds to low frequency were not obtained because of interference by CM. Locations along the surface of the basilar membrane were identified by percent distance from apex, and can be related to the physiological data because sound is encoded in a tonotopic fashion with the highest frequencies represented in the most basal portion of the cochlea. Both inner hair cells (IHCs) and outer hair cells (OHCs) within the most apical 40% of the basilar membrane showed normal SDH (succinate dehydrogenase) staining. For example, FIG. 7A is an image of the hair cells located at 26% of the basilar membrane. The remaining 60%, FIG. 7B, of the basilar membrane showed hair cell damage. At 74%, FIG. 7C, the loss of OHCs and IHCs occurs. Interestingly, at some places very close to the base where all IHCs were gone, many OHCs were still surviving (FIG. 7D, 90%). That CM sensitivity was normal (FIG. 7F) indicates normal function in the surviving OHCs in the basal turn close to the round window.

Example 4

L-DFMO and D-DFMO Toxicity and Ototoxicity in Guinea Pigs

Figure 8:
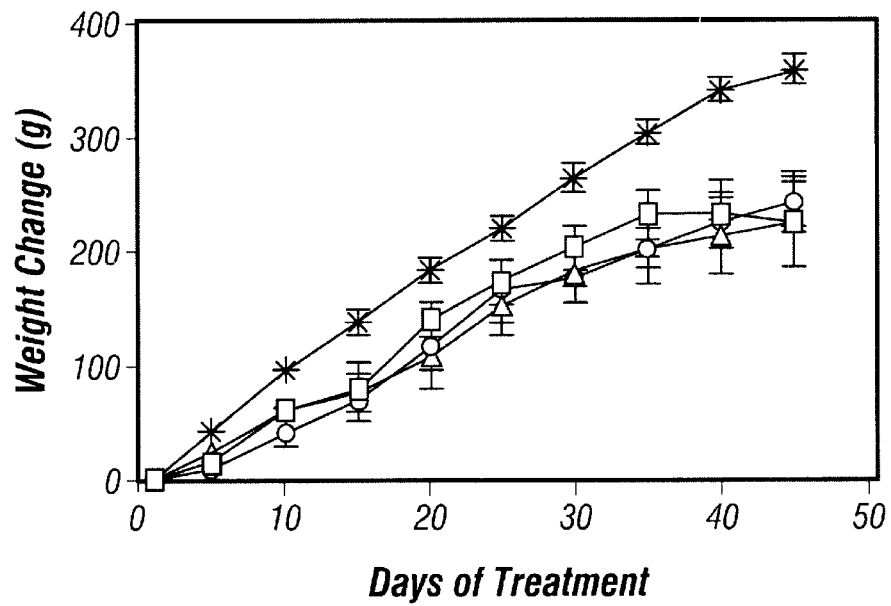
FIG. 8 Weight gain of guinea pigs treated with 1 g/kg D,L-DFMO, D-DFMO or L-DFMO by ip injection daily for 45 days. All animals survived until auditory testing. ★: Control (n=5), ■: 1 g/kg D,L-DFMO (n=5), ★: 1 g/kg D-DFMO (n=5), and ▲: 1 g/kg L-DFMO (n=5). Vertical bars are standard error (SE).
Figure 9A:
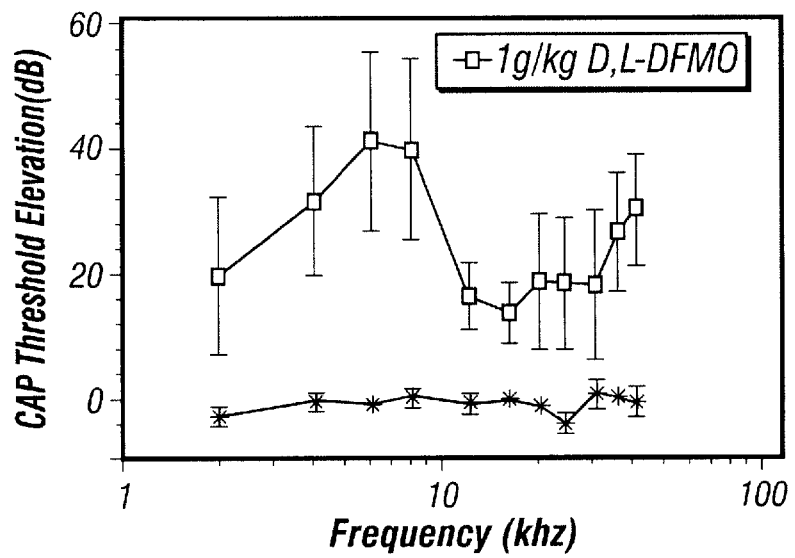
FIG. 9 CAP threshold elevation of guinea pigs caused by treatment with 1 g/kg D,L-DFMO, D-DFMO or L-DFMO by ip injection daily. The animals are the same as in FIG. 8. (A) ★: Control (n=5) and ■: 1 g/kg D,L-DFMO (n=5); (B) ★: Control (n=5) and ●: 1 g/kg D-DFMO (n=5); (C) ★: Control (n=5) and ▲: 1 g/kg L-DFMO (n=5). Vertical bars are standard error (SE).
Figure 9B:
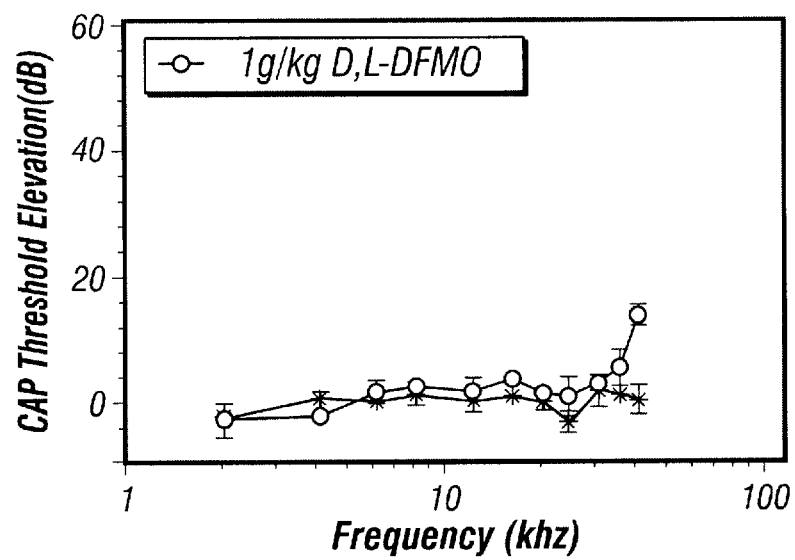
Figure 9C:
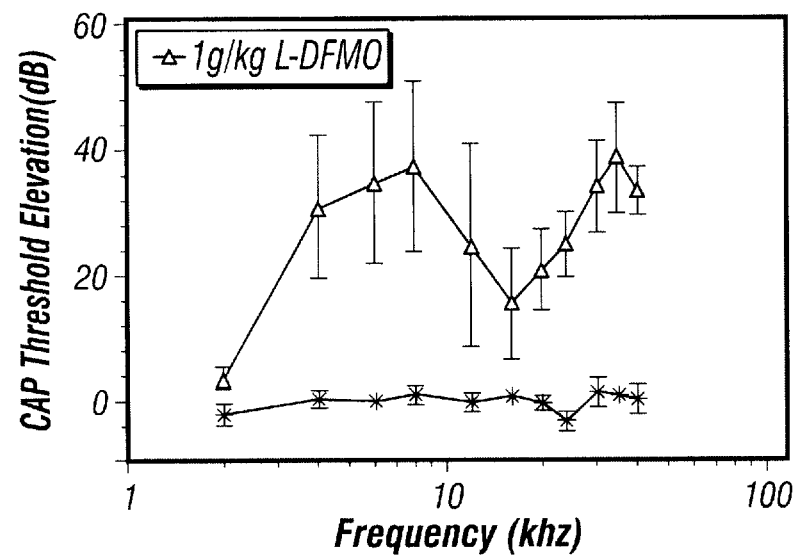
Figure 10A:
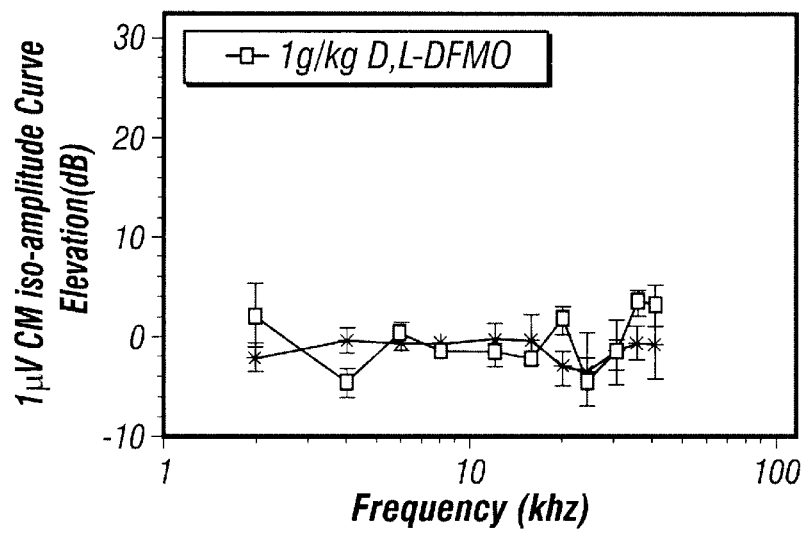
FIG. 10A, FIG. 10B, and FIG. 10C Elevations of 1 $\mu$V RMS CM iso-amplitude curve of guinea pigs caused by treatment with 1 g/kg D,L-DFMO, D-DFMO or L-DFMO by ip injection daily. The animals are the same as in FIG. 8.
Figure 10B:
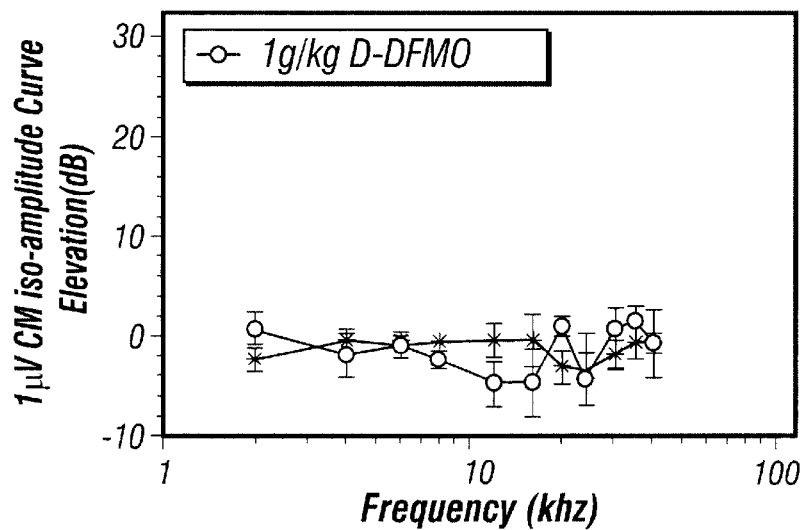
Figure 10C:
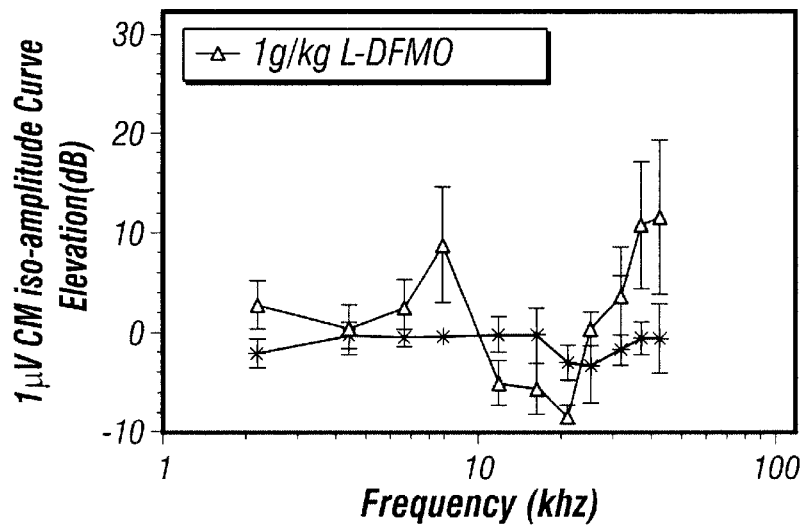

Data comparing the enantiomers of DFMO and the racemate are shown in FIG. 8. FIG. 9 AND FIG. 10. It was found that D-DFMO does not produce any significant hearing impairment in the guinea pig whereas the L-enantiomer of DFMO generates a threshold shift that surpassed that of the D,L-DFMO treatment. The weight data suggest that the enantiomers do not produce significant general toxicity.

FIG. 8 shows the growth of the animals. Although the treated animals appeared to grow at a slower rate than the controls, statistical analysis of the data for the entire trial period showed no significant difference ($F_{[3,16]}=0.95$, p=0.44). The weight gain between the enantiomers and racemate did not differ from each other.

FIG. 9 shows the CAP threshold shifts for the enantiomer, racemate and controls. Both L-DFMO (filled triangle) and the D,L-DFMO (filled square) generated an average threshold shift of 25±2 dB. When the D-enantiomer (FIG. 9, filled circle) was measured for auditory function, a CAP threshold average shift of 2 dB was found over all frequencies with a slight elevation at 40 kHz. Repeated measures ANOVA determined a significant difference in CAP between the four dose groups receiving 1 g/kg/day D,L-DFMO, 1 g/kg/day/day D-DFMO, 1 g/kg/day L-DFMO, and saline (between treatment, $F_{[3,19]}=7.41$, p=0.002; between frequency, $F_{[10,190]}=7.99$, p<0.001; treatment-frequency interaction, $F_{[30,190]}=2.90$, p<0.001). When subjected to Fisher's LSD, the L-DFMO (p<0.005) and D,L-DFMO (p<0.005) were found to be significantly different from the control over all test frequencies, but the D-enantiomer was not.

In contrast to the significant effect on CAP thresholds, L-DFMO did not generate change of CM sensitivity (FIG. 10, filled triangle). The slight elevation at 35 and 40 kHz is due to one animal showing as much as a 40 dB loss at these two frequencies. D-DFMO also did not alter the CM. None of the treatments effects on CM were significant from the control ($F_{[3,16]}=0.92$, p=0.45).

Discussion

When treating animals with an enzyme inhibitor, one would expect the results to be a dose dependent curve with some saturation point. For ototoxicity to be eliminated as a side effect of D,L-DFMO chemotherapy, it is necessary to determine an ototoxic dose response for this drug. Previous studies had given the drug in drinking water, which made for a difficult determination of actual drug intake. Therefore, direct delivery of the drug is needed to elicit an accurate ototoxic dose response. Both the rat and guinea pig are utilized in this process.

The rat model generated no significant weight loss (toxicity) and no significant threshold shifts (ototoxicity) over the audiometric range. The results imply that D,L-DFMO treatment in rats does not produce the ototoxic side effects previously reported in human cancer patients. Schweitzer et al. (1986) found that treating rats with 1% DFMO in the drinking water (approximately 300 mg/kg assuming a daily intake of 30 ml water) not only resulted in normal brainstem evoked potentials, but the levels of polyamines were not depleted to a level considered disrupting in other systems. The inventors extended this data by exposing the animals, by intubation, to much greater doses, up to 4 times, and still found no effect on auditory thresholds. If the levels of polyamines do play a role in auditory function, the metabolism of the rat is such that D,L-DFMO does not inhibit polyamine synthesis to a critical level and therefore the rat cannot be used as a reliable model for determination of D,L-DFMO ototoxicity.

In contrast, D,L-DFMO treatment in the guinea pig generates significant auditory dysfunction (ototoxicity). Again, determination of actual drug intake from previous studies was difficult and therefore all drug administration in the current study was by ip injection. Within the first six days of the study, D,L-DFMO showed substantial toxicity at 3 g/kg/day with 100% of the animals dying. The remaining treatment groups did not produce significant toxicity (mortality or weight loss) within the trial period. Necropsies were carried out on one animal that died during the course of treatment and on the subjects that survived until the end of the experiment. The reports support the conclusion that repeated injection was not responsible for the subject's death or for depression in weight gain.

The CAP thresholds showed that D,L-DFMO produces a significant and reproducible shift in the guinea pig. As expected, the average threshold shift across test frequencies is dose dependent. The ability of the 2 g/kg/day D,L-DFMO to generate a greater auditory impairment in a shorter period of time implies that the amount of drug given, and not the duration of the treatment, ultimately determines the ototoxicity.

CM is generated mainly by the outer hair cells in the basal turn of the cochlea and is a sensitive measurement for detecting impairment following many ototoxic drugs including the aminoglycoside and cisplatin, but D,L-DFMO did not generate a change in the CM iso-amplitude curve. Histology revealed that the majority of outer hair cells at the very basal turn were intact accounting for the null effect on CM. The basal inner hair cells, however, showed extensive damage with a majority missing. The middle of the cochlea showed both damage and loss of outer and inner hair cells. At the apex, neither outer nor inner hair cells were damaged or missing. Therefore, D,L-DFMO may have some preference for hair cells located at the basal turns of the cochlea.

The generation of the dose response data allowed for comparison of D,L-DFMO and its enantiomers. Since the inventors found a reproducible D,L-DFMO induced threshold shift in the guinea pig, the characterization of the enantiomers was continued in the guinea pig. Due to the lethality of the high doses, 1 g/kg/day was chosen for comparison of the enantiomers with the racemate.

The enantiomers did not show significant toxicity (determined by weight gain). The D-form of DFMO was found to have no significant effects on either the compound action potential or cochlear microphonic. Evaluation of auditory function found that the L-form of DFMO produced significant disruption of normal cochlear potentials. The research described above may have implications for the development of chemotherapeutic strategies involving a single enantiomer of DFMO.

Example 5

Comparison of D-, L-, and DL-Difluoromethylornithine. Effects on Ornithine Decarboxylase (ODC) Activity Materials and Methods Recombinant murine ODC was expressed in *E coli* and purified for the studies. A microassay is used to measure ODC activity and inhibition by DFMO. Specifically, 20 ul of recombinant murine ODC at a concentration of 0.6 mg/ml was preincubated with serial dilutions (0 to 80 uM of D-, L-, or D-L-DFMO) in a 1.5 ml Eppendorf tube for 30 minutes at room temperature. The enzymatic reaction was initiated in the Eppendorf tube by the addition of 27.5 ul of Brij 35 ODC assay mixture (final concentrations: 40 mM Tris HCl pH 7.5, 8 mM DTT, 0.64 mM pyridoxal phosphate (PLP), 0.80 mM EDTA, 0.04% Brij 35 and 0.2 uCi ($^{14}$C) L-ornithine). 40 ul of the $CO_2$ trapping agent (ethanolamine/3-methoxyethanol, 2:1) was placed at the bottom of a 20 ml glass scre-cap liquid scintillation vial and the open Eppendorf tube containing the sample was placed in the vial away from the trapping agent. The scintillation vial was immediately capped with a septum cap and the vials were incubated in a 37° shaking water bath for 1 hour. The vials were then removed from the water bath and 100 ul of 2M citric acid was added through the septum into the open Eppendorf tube to stop the ODC reaction. The scintillation vials were incubated for an additional 2 hours at 37° to quench the reaction. The tubes were removed from the vials and 6 ml of scintillation fluid was added. The vials were counted on a Beckman LS-6500 scintillation counter for 1 minute. $K_i$ inhibition values were obtained by a least-squares fit of the data.

Results

In three separate studies using concentrations from 0.6 uM to 80 uM D-, L-, and D,L-DFMO, the effective concentration level of each which inhibits 50% of the ODC activity ($K_i$) was determined. The effective concentration levels are as follows:

| D-DFMO | 24.1 uM |
|---|---|
| L-DFMO | 6.4 uM |
| D,L-DFMO | 8.1 uM |

Both enantiomers, as well as the racemic mixture, were inhibitory. The $K_i$ of D-DFMO was four fold lower than the L-form and 3 fold lower than the mixture.

Example 6

Induction of Apoptosis in Cell Lines by D-, L-, and D,L-DFMO

The ability of D-, L-, and D,L-DFMO to induce apoptosis was examined in six human cell lines: MCF-7 (breast cancer, ATCC #HTB22), LNCaP (prostate cancer, ATCC #CRL1740), PC-3 (prostate cancer, ATCC #CRL1435), HT-29 (colon cancer, ATCC #HTB38), HSK 612 (normal karatinocytes, purchased from InCell, Inc.) and 506SM (normal colon submucosal mesenchymal cells, purchased from InCell, Inc.). Each of the three forms of DFMO were tested at two concentrations (1 and 10 uM). Adriamycin and calcium chloride were used as positive controls. Apoptosis was assayed using a multi-well plate DNA fragmentation assay according to the Cellular DNA Fragmentation ELISA kit (Boehringer Mannheim Biochemicals, Cat. #1585–045) and Hoechst staining.

All three forms of DFMO caused apoptosis but not cytotoxicity in the cancer cell lines. There was no overall major difference between the forms of DFMO at the concentrations examined. Apoptosis was more pronounced for all the DFMO solutions than for the adriamycin positive control (which was cytotoxic as well as apoptotic).

Example 7

In Vivo Evaluation of the Enantiomers of DFMO in the MCF-7 Human Breast Cancer Xenograft Model Nude mice were implanted with the estrogen-dependent human breast tumor line, MCF-7 (ATCC #HTB22). D-, L-, or D,L-DFMO were administered ad libidum in the animals' drinking water as 0.5% w/v solutions, with eight animals per group. One additional group of eight animals were administered D,L-DFMO as a 3.0% solution. The experiment was terminated on Day 90 (when control tumors had reached a size of 400 mg.). Mice were weighed twice weekly, and tumor measurements were taken by calipers twice weekly, starting at time of DFMO administration (Day 1). Tumor measurements were converted to mg tumor weight by the formula, $L^2 \times W/2$.

Figure 11:
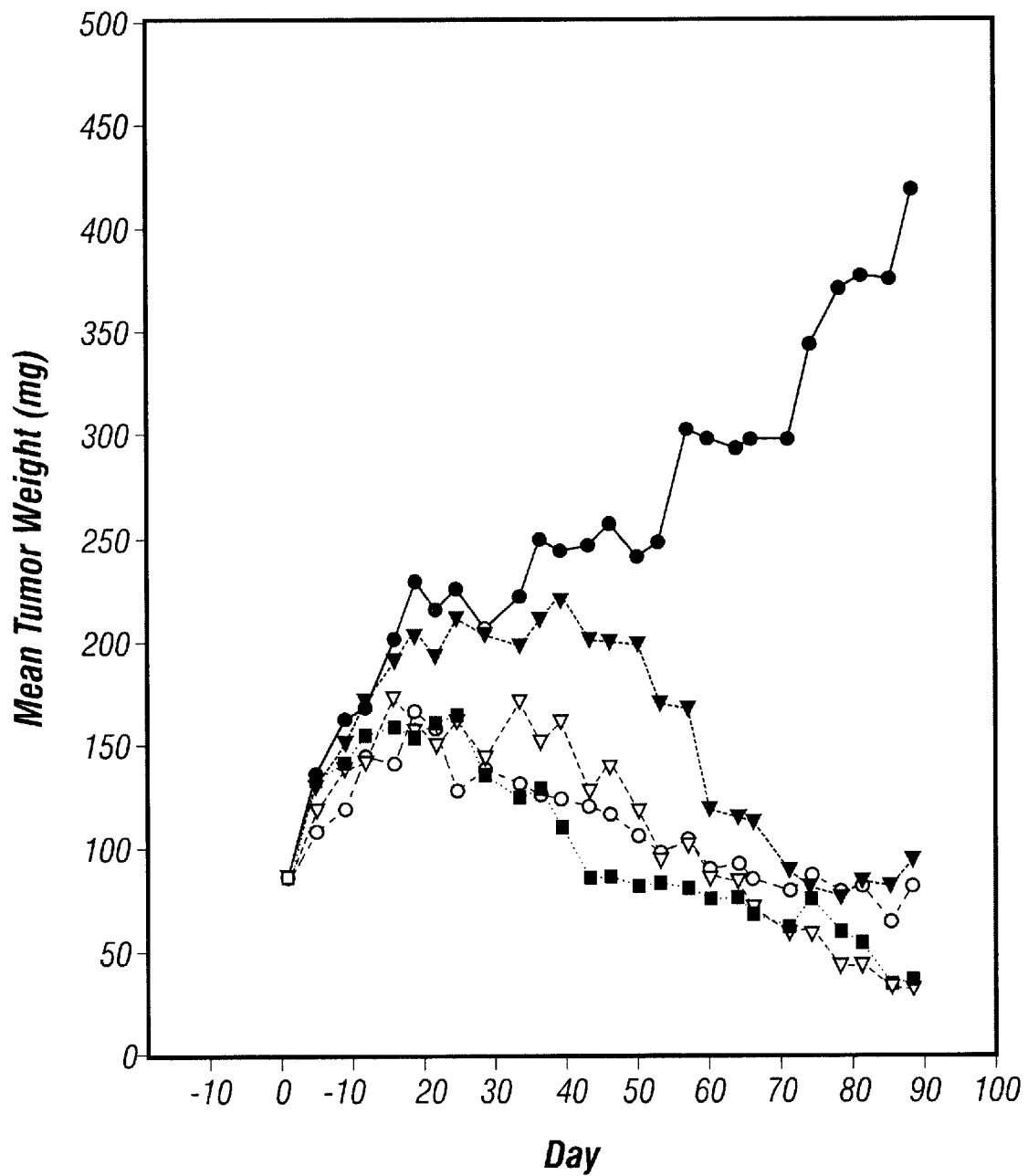
FIG. 11 Mean Tumor weight of MCF-7 human breast tumors in nude rats. D-, L-, or D,L-DFMO were administered ad libidum in the animals' drinking water at the following concentrations: 0.0% controls (●);0.5% D-DFMO (○); 0.5% L-DFMO (▼); 0.5% D,L-DFMO (▽); 3.0% D,L-DFMO (■).

For the group receiving D,L-DFMO, seven of eight animals experienced mean partial tumor shrinkage of 60.4%, with a tumor growth inhibition of 99.2% in the eighth animal. For the group receiving L-DFMO, seven of eight animals experienced a mean partial tumor shrinkage of 50.0%, with a tumor growth inhibition of 5.5% in the eighth animal. For the group receiving D-DFMO, four of eight animals experienced a mean partial tumor shrinkage of 62.6%, two of eight animals had a tumor inhibition of 84.7%, and the remaining two animals experienced toxic death. The averaged results of each group compared to controls, including the 3.0% D,L-DFMO group, are shown in FIG. 11. Differences in antitumor activity seen in the groups are not considered significant.

Example 8

Effects of Enantiomers of DFMO on Ornithine Decarboxylase In Vitro Activity

Two in vitro systems were examined for the effects of D-, L-, or D,L-DFMO to inhibit ornithine decarboxylase (ODC). The first utilized ODC synthesized in a cell free system from a mouse ODC cDNA. L-DFMO was found to be a more potent ODC inhibitor at low inhibitor:substrate ratios than D-DFMO. The D isomer was estimated to be 10 fold less potent than the L-form in this system, while the racemic D,L-DFMO was intermediate in potency. The L-form appeared to be acting in a non-competitive manner (as would be expected for an irreversible inhibitor) whereas the D-form appears to be acting in a competitive manner.

The second system looked at inhibition of endogenous ODC in HCT-116 colon cancer-derived cells. Again, the L-form was more potent than the D-form in reducing intracellular polyamine levels, the end product of ODC activity. All forms of DFMO suppressed putrescine levels, another end product of ODC, below the limit of detection. Polyamine levels recovered more quickly in the cells treated with D-DFMO than in cells treated with L-DFMO.

Example 9

Comparison of In Vivo Inhibition of ODC by D-, L-, and D,L-DFMO

Figure 12:
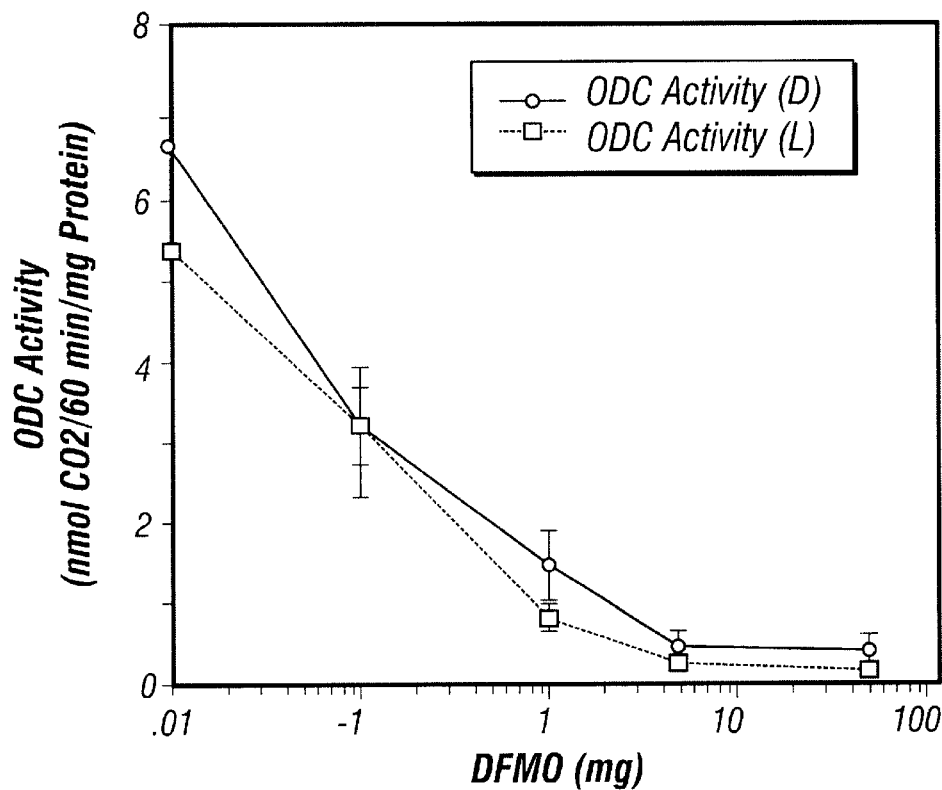
FIG. 12 A dose-response study to compare the relative inhibitory activity of D- and L-DFMO isomers. The indicated doses of DFMO were given only once orally by gavage to a group of female mice. TPA (5 nmol) in 0.2 ml acetone was applied to the shaved backs of mice 1 hour post-DFMO treatment. There were three mice per treatment group. Soluble epidermal ODC activity was determined 5 hr after TPA application. Each value is the mean±S.E. of the duplicate determinations of ODC activity from epidermal extract prepared from three mice.

The ability of systemically administered D-, L-, and D,L-DFMO to inhibit phorbol ester induced ODC in mouse skin. All forms of DFMO given at 100 mg (either in a single dose or split doses) completely inhibited ODC activity. 5 mg doses of all forms given daily for five days nearly completely inhibited ODC activity, with no difference between the isomers. As shown in FIG. 12, a single dose of D-DFMO versus L-DFMO showed a dose-dependent inhibition of ODC, again with no difference seen between the two isomers.

Example 10

Analysis of D,L-DFMO in Biological Fluids

Figure 13:
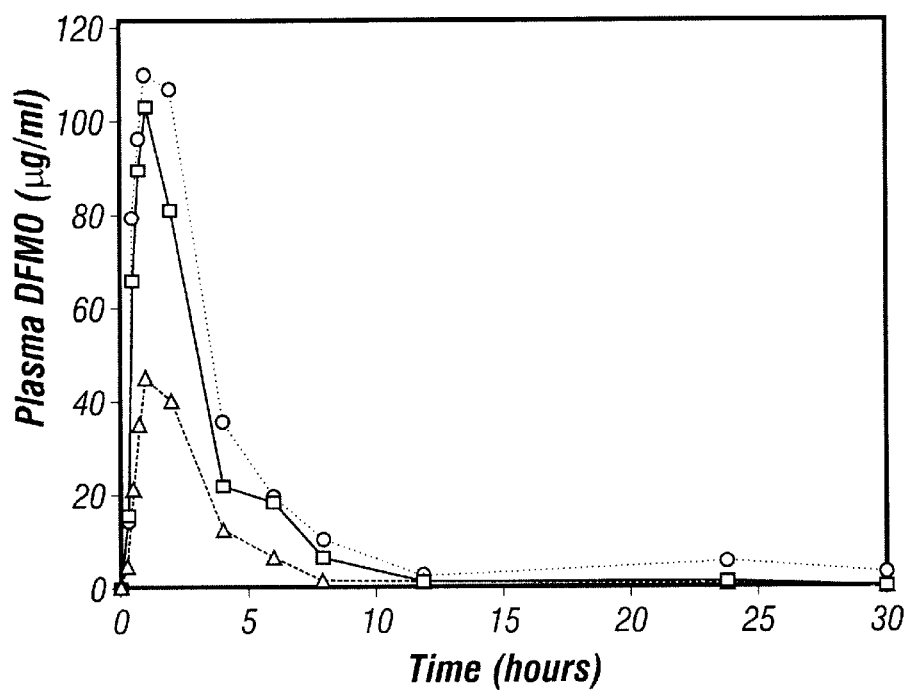
FIG. 13 Mean plasma levels of rats receiving orally 400 mg/kg racemic D,L-DFMO (○), 200 mg/kg D-DFMO (■), or 200 mg/kg L-DFMO (▲).

Rats were given single doses of D-, L-, or D,L-DFMO and plasma levels determined over time (FIG. 13). Rats given 400 mg/kg of D,L-DFMO achieved a maximum plasma level of 109 ug/ml between one and two hours after administration. Rats receiving either D-DFMO or L-DFMO at 200 mg/kg achieved plasma levels of 102 ug/ml and 45 ug/ml respectively over the same time course. The lower blood levels seen with L-DFMO may be due to a lower bioavailability for this form, more rapid excretion, or more rapid binding to tissues or proteins.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bachrach, "Function of naturally occurring polyamines," Academic Press, 1973.
Bussey, "Historical developments in familial adenomatous polyposis," In:: Lemuel Herrera (ed), Familial Adenomatous Polyposis, pp. 1–22, Alan R. Liss, Inc. New York, 1990.
Canellakis, Viceps-Madore, Kyriakidis, Heller, "The regulation and function of ornithine decarboxylase and of the polyamines," In: Current Topics in Cellular Regulation, Academic Press, 15:155–202, 1979.
Croghan, Aickin, Meyskens, "Dose-Related α-Difluoromethylornithine Ototoxicity," Am. J. Clin. Oncol., 14(4):331–335, 1991.
Danzin, Ducep, Schirlin, Wagner, "Absence of stereospecificity in the suicide inhibition of ornithine decarboxylase," Biochemistry of Vitamin $B_6$, 333–336, 1987.
Giardiello, Hamilton, Hylind, Yang, Tamez, Casero, "Ornithine decarboxylase and polyamines in familial adenomatous polyposis," Cancer Res., (57):199–201, 1997.
Kingsnorth, King, Diekema, McCann, Ross, Malt, "Inhibition of ornithine decarboxylase with 2-difluoromethylornithine: reduced incidence of dimethylhydrazine-induced colon tumors in mice," Cancer Res., (43):2545–2549, 1983.
Lipkin, "New rodent models for studies of chemopreventive agents," J Cell Biochem Suppl (28–29):144–7, 1997.
Lowy, Willumsen, "Function and regulation of ras," Annu Rev Biochem (62):851–91, 1993.
Luc and Baylin, "Inhibition of intestinal epithelial DNA synthesis and adaptive hyperplasia after jejunectomy in the rat by suppression of polyamines biosynthesis," J. Clin. Invest. 74:698–704, 1984.
Marks, Mattox, Casero, "The effects of DFMO on polyamine metabolism in the inner ear," Hear. Res. 53(2):230–236, 1991.
Messing, Verma, Storer, Sansiman, Bram, "Ornithine decarboxylase (ODC) activity in normal and malignant urothelium—Implications for prevention and treatment of bladder cancer (BC)," Proc. Amer. Urological Assoc. 153, Supplement 523A, Abstract #1177, 1995.

Meyskens, Jr. and Gerner, "Development of difluoromethylornithine as a chemoprevention agent for the management of colon cancer," *J. Cell. Bio.*, 22:126–131, 1995.

Meyskens, Jr., Emerson, Pelot, Meshkinpour, Shassetz, Einsphar, Alberts, Gerner, "Dose de-escalation chemoprevention trial of α-difluoromethylornithine in patients with colon polyp," *J. Natl. Cancer Inst.* 86(15):1122–1130, 1994.

Oka, Perry, Takemoto, Sakai, Terada, Inoue, "The multiple regulatory roles of polyamine in the hormonal induction of mammary gland development," *In: Advances Polyamine Research.* 3:309–320, 1981

Pasic, Heisey, Love, "α-Difluoromethylornithine ototoxicity: chemoprevention clinical trial results," *Arch. Otolaryngol. Head Neck Surg.* 123(12):1281–1286, 1997.

Pegg, "Recent advances in the biochemistry of polyamines in eukaryotes," *Biochem. J.* 234, 249–262, 1986.

Pegg, and McCann, "Polyamine metabolism and function," *Am. J. Physiol.* 243: 212–221, 1982.

Salzer, Mattox, Brownell, "Cochlear damage and increased threshold in α-difluoromethylornithine (DFMO) treated guinea pigs," *Hear. Res.* 46:101–112, 1990.

Schweitzer, Casseday, Sjoerdsma, McCann, Bartolome, "Identification of polyamines in the cochlea of the rat and their potential role in hearing," *Brain Research Bulletin*, 16:215–218, 1986.

Su, Kinzler, Vogelstein, Preisinger, Moser, Luongo, Gould, Dove, "Multiple intestinal neoplasia caused by a mutation in the murine homolog of the APC gene," *Science*, (256):668–670, 1992.

Tempero, Nishioka, Knott, Zetterman, "Chemoprevention of mouse colon tumors with difluromethylornithine during and after carcinogen treatment," *Cancer Res.*, (49):5793–5797, 1989.

Thet, Parra, Shelburne, "Repair of oxygen-induced lung injury in adult rats: The role of ornithine decarboxylase and polyamines," *Am. Rev. Respir. Dis.* 129, 174–181, 1984.

Wagner, Gaget, Heintzelmann, Wolf "Resolution of the enantiomers of various alpha-substituted ornithine and lysine analogs by high-performance liquid chromatography with chiral eluant and by gas chromatography on Chirasil-Val," *Anal Biochem* 164(1):102–16, 1987.

Williams-Ashman, and Canellakis, "Polyamines in mammalian biology and medicine," *Prespective Biol. Med.* 22:421–453, 1979.

What is claimed is:

1. A method for preventing and/or treating a tumor sensitive to difluoromethylornithine (DFMO) in a patient in need thereof comprising administering an effective amount of substantially enriched D enantiomer of DFMO (D-DFMO) or an analog thereof to said patient and wherein the substantially enriched D enantiomer comprises at least 70% by weight of the total difluoromethylornithine or analog and wherein the enriched D enantiomer has reduced ototoxicity.

2. The method of claim 1, wherein D-DFMO or an analog thereof is administered at a dose of about 0.05 to about 20.0 gm/M$^2$/day.

3. The method of claim 2, wherein D-DFMO or an analog thereof is administered at a dose of about 0.1 to about 2.0 gm/M$^2$/day.

4. The method of claim 1, wherein the tumor being prevented or treated is selected from a bladder tumor, a colon tumor, a breast tumor, a pancreatic tumor, a brain tumor, a lung tumor, a stomach tumor, a skin tumor, a testicular tumor, a prostate tumor, an ovarian tumor, a liver tumor, a esophageal tumor, and any combination thereof.

5. The method of claim 1, wherein the tumor is a colon tumor.

6. The method of claim 5, wherein the colon tumor is familial adenomatous polyposis.

7. The method of claim 1, wherein the tumor is a bladder tumor.

8. The method of claim 7, wherein the bladder tumor is a superficial bladder tumor.

9. The method of claim 1, wherein said preventing and/or treating tumor is accomplished by a mechanism selected from inducing apoptosis, inhibiting cell division, inhibiting metastatic potential, reducing tumor burden, increasing sensitivity to chemotherapy or radiotherapy, killing a tumor cell, inhibiting the growth of a tumor cell, inducing tumor regression and any combination thereof.

10. The method of claim 1, wherein D-DFMO or an analog thereof is administered at least a second time.

11. The method of claim 1, further comprising resection of said tumor.

12. The method of claim 11, wherein D-DFMO or an analog thereof is administered prior to said resection.

13. The method of claim 11, wherein DFMO or an analog thereof is administered after said resection.

14. The method of claim 1, wherein administration route is selected from oral, intravenous, intramuscular, intratumoral, intraperitoneal, intradermal, dermal, nasal, rectal, vaginal, topical, buccal, and intralymphatic administration.

15. The method of claim 1, wherein DFMO or an analog thereof is administered directly to said tumor.

16. The method of claim 1, wherein D-DFMO or an analog thereof is administered systemically.

17. The method of claim 1, wherein D-DFMO or an analog thereof is administered into the regional vasculature of said tumor.

18. The method of claim 1, wherein D-DFMO or an analog thereof is administered into the region lymph system of said tumor.

19. The method of claim 1, wherein D-DFMO or an analog thereof is administered orally.

20. The method of claim 1, wherein the D enantiomer comprises at least 80% by weight of the difluoromethylornithine or analog dosage being administered.

21. The method of claim 1, wherein the D enantiomer comprises at least 90% by weight of the difluoromethylornithine or analog dosage being administered.

22. The method of claim 1, wherein the D enantiomer comprises at least 95% by weight of the difluoromethylornithine or analog dosage being administered.

23. The method of claim 1, wherein the D enantiomer comprises at least 97.5% by weight of the difluoromethylornithine or analog dosage being administered.

24. The method of claim 1, wherein the D enantiomer comprises at least 99% by weight of the difluoromethylornithine or analog dosage being administered.

25. The method of claim 1, wherein the D enantiomer comprises at least 99.5% by weight of the difluoromethylornithine or analog dosage being administered.

26. A pharmaceutical composition, comprising substantially enriched D enantiomer of difluoromethylornithine (D-DFMO) or analog thereof together with a pharmaceutically acceptable carrier and wherein the substantially enriched D enantiomer comprises at least 70% by weight of the total difluoromethylornithine or analog and wherein the enriched D enantiomer has reduced ototoxicity.

27. The pharmaceutical composition of claim 26, formulated in a form selected from rapid release, timed release, delayed release, sustained release, oral suspension, tablet, capsule, powder, troche, suppository, liposome, nanoparticle, inhalant, nasal solution, ophthalmic solution, otic solution, irrigation solution, intravenous admixture, epidermal or transdermal solution, buccal tablet, syrup, cream, ointment, lotion, gel, emulsion, elixer, douche, enema, gargle, implant, and aerosol.

28. The pharmaceutical composition of claim 26, wherein the D enantiomer comprises at least 80% by weight of the total difluoromethylornithine or analog.

29. The pharmaceutical composition of claim 26, wherein the D enantiomer comprises at least 90% by weight of the total difluoromethylornithine or analog.

30. The pharmaceutical composition of claim 26, wherein the D enantiomer comprises at least 95% by weight of the total difluoromethylornithine or analog.

31. The pharmaceutical composition of claim 26, wherein the D enantiomer comprises at least 97.5% by weight of the total difluoromethylornithine or analog.

32. The pharmaceutical composition of claim 26, wherein the D enantiomer comprises at least 99% by weight of the total difluoromethylornithine or analog.

33. The pharmaceutical composition of claim 26, wherein the D enantiomer comprises at least 99.5% by weight of the total difluoromethylornithine or analog.

* * * * *